United States Patent
Shu

(10) Patent No.: US 11,155,561 B2
(45) Date of Patent: Oct. 26, 2021

(54) SUBSTITUTED GLUTARIMIDES AS BTK INHIBITORS

(71) Applicant: SHANGHAI MEIZER PHARMACEUTICALS CO., LTD., Shanghai (CN)

(72) Inventor: Yongzhi Shu, Shanghai (CN)

(73) Assignee: SHANGHAI MEIZER PHARMACEUTICALS CO., LTD., Shanghai (CN)

(*) Notice: Subject to any disclaimer, the term of this patent is extended or adjusted under 35 U.S.C. 154(b) by 0 days.

(21) Appl. No.: 16/808,338

(22) Filed: Mar. 3, 2020

(65) Prior Publication Data

US 2020/0199132 A1 Jun. 25, 2020

Related U.S. Application Data

(63) Continuation of application No. PCT/CN2018/103710, filed on Sep. 2, 2018.

(30) Foreign Application Priority Data

Sep. 3, 2017 (CN) .......................... 201710783076.X

(51) Int. Cl.
- *A61K 31/4412* (2006.01)
- *C07D 211/40* (2006.01)
- *C07D 487/04* (2006.01)
- *A61P 35/00* (2006.01)

(52) U.S. Cl.
CPC ............ *C07D 487/04* (2013.01); *A61P 35/00* (2018.01)

(58) Field of Classification Search
CPC .......................... A61K 31/4412; C07D 211/40
USPC ........................................... 514/348; 546/296
See application file for complete search history.

(56) References Cited

FOREIGN PATENT DOCUMENTS

| WO | 2017117473 A1 | 7/2017 | |
|----|---------------|--------|---|
| WO | 2018098288 A1 | 5/2018 | |
| WO | WO-2019127008 A1 * | 7/2019 | ............ A61P 35/00 |

OTHER PUBLICATIONS

International Search Report (in Chinese and English) and Written Opinion issued in PCT/CN2018/103710, dated Dec. 4, 2018, 19 pages provided.

Buhimschi et al., "Targeting the C481S Ibrutinib-Resistance Mutation in Bruton's Tyrosine Kinase Using PROTAC-Mediated Degradation", Biochemistry, vol. 57, Downloaded from http://pubs.acs.org on May 31, 2018, 40 pages provided.

Deng et al., "Research progress on Btk inhibitors", Journal of Pharmaceutical Research, vol. 33, No. 6, 2014, with English Abstract, 4 pages provided, cited in Specification.

International Preliminary Report on Patentability issued in PCT/CN2018/103710, dated Dec. 12, 2019, 4 pages sprovided.

* cited by examiner

*Primary Examiner* — Douglas M Willis
(74) *Attorney, Agent, or Firm* — Hamre, Schumann, Mueller & Larson, P.C.

(57) ABSTRACT

A compound for inhibiting and degrading Bruton's tyrosine kinase (Btk) is disclosed. The compound is a substituted glutarimide represented by Formula I'. The compound can be used in the preparation of drugs for treating Btk activity-related diseases.

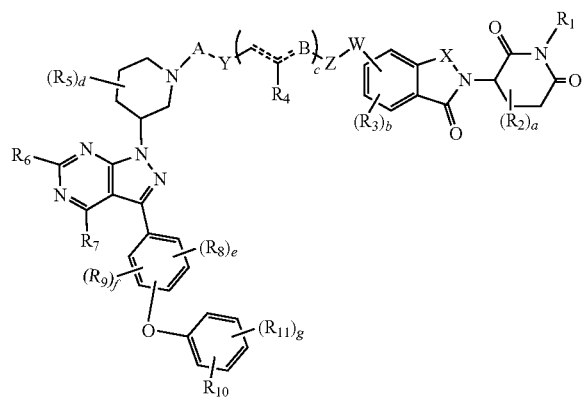

Formula I'

13 Claims, No Drawings

SUBSTITUTED GLUTARIMIDES AS BTK INHIBITORS

TECHNICAL FIELD

The present invention belongs to the field of medicine, and particularly relates to a class of compounds having the activity of degrading tyrosine protein kinase Btk, and preparation and application thereof.

BACKGROUND

Btk, i.e. Bruton's tyrosine kinase, is a member of the Tec family of non-receptor tyrosine kinases. It is an essential gene for cell differentiation and proliferation, and is expressed in B-cell lymphoma, acute lymphoblastic leukemia (ALL) and plasmacytoma. Btk is a key component of the B cell receptor (BCR) signaling pathway and is a good site for targeted treatment of diseases such as B-cell lymphoma.

Btk is a key regulator of B cell development, activation, signaling and survival, and is involved in the regulation of angiogenesis, cell proliferation and apoptosis, and cell movement. In addition, Btk is also involved in many other hematopoietic cell signaling pathways, such as participating in Toll-like receptors and cytokine receptor mediated signaling pathways in macrophages, and participating in IgE receptor signaling in mast cells.

Recent studies have shown that Btk signaling pathway is a new hotspot currently in clinical treatment research for non-Hodgkin's lymphoma (NHL), especially chronic lymphocytic leukemia (CLL), B-cell lymphoma and autoimmune diseases (rheumatoid arthritis, psoriasis, etc.) (Deng Rong, Zhao Lizhi. Research progress of Btk inhibitors. Pharmaceutical Research, 2014, 33 (6): 359-372).

Therefore, those skilled in the art are committed to developing compounds capable of inhibiting Btk activity.

SUMMARY OF THE INVENTION

The object of the present invention is to provide a compound capable of inhibiting and degrading Btk, and preparation and application thereof.

In the first aspect of the present invention, there is provided a compound represented by the following formula I, or a pharmaceutically acceptable salt thereof:

wherein,
— refers to a single bond;
------- refers to a single or double bond;
A is missing or selected from $C(=O)$, $C(=O)X1$, $SOX1$, $SO_2X1$, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); wherein X1 is missing or selected from $(CR_{12}R_{13})_jO$, $(CR_{12}R_{13})_j$, 3- to 8-membered heteroaromatic ring (preferably, such as pyridyl, or 1,2,3-triazolyl) with or without substituent(s), 3- to 8-membered aromatic ring (preferably, such as phenyl) with or without substituent(s), and $NR_{14}$; wherein $R_{12}$, $R_{13}$, $R_{14}$ is each independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); j is an integer between 0 and 3;

W is missing or selected from O, $NR_{17}$, $-X2C(=O)X3$, $-X2S(=O)_gX3$; wherein R17 is independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); wherein X2, X3 is each independently missing or selected from O, S, and $NR_{18}$; wherein g is an integer between 0 and 2; wherein $R_{18}$ is independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Y is $(CR_{22}R_{23})_h$, $CHX4(CR_{22}R_{23})_h$, $CX4=CH(CR_{22}R_{23})_h$, $C(=CH2)(CR_{22}R_{23})_h$ or $(CR_{22}R_{23})_h$; wherein h is an integer between 0 and 30; wherein $R_{22}$, $R_{23}$ is each independently H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), or $C_{1-8}$ hydrocarbyloxy group with or without substituent(s); wherein X4 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without sub-

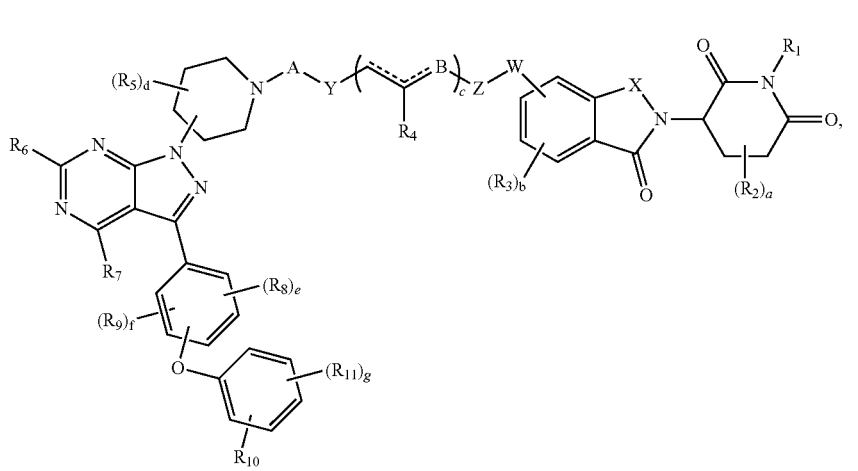

I stituent(s), $C_{1-8}$ cyclic hydrocarbyl group with or without substituent(s), or $C_{1-8}$ heterocyclic hydrocarbyl group with or without substituent(s);

Z is $(CR_{24}R_{25})_i$, $CHX5(CR_{24}R_{25})_i$, $CX5=CH(CR_{24}R_{25})_i$ or $C\equiv C(CR_{24}R_{25})_i$; wherein i is an integer between 0 and 30; wherein $R_{24}$, $R_{25}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X5 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

B is missing or selected from O, C=O, S, $NR_{15}$, $-NR_{15}C(=O)-$, $-C(=O)NR_{15}-$, $-C(=O)O-$, $OC(=O)O-$, $-NR_{15}C(=O)O-$, $-OC(=O)NR_{15}-$, $-NR_{15}C(=O)NR_{16}-$, $C_{1-12}$ hydrocarbyl group with or without substituent(s), $C_{1-12}$ cyclic hydrocarbyl group with or without substituent(s), and $C_{1-12}$ heterocyclic hydrocarbyl group with or without substituent(s); wherein $R_{15}$, $R_{16}$ is each independently selected from H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

X is selected from $CR_{19}R_{20}$, $C(=O)$, $S(=O)$, $SO_2$, and $NR_{21}$; wherein $R_{19}$, $R_{20}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), or $C_{1-8}$ hydrocarbyloxy group with or without substituent(s); wherein $R_{21}$ is selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_1$ is selected from H, $C_{1-8}$ hydrocarbyl group with or without substituent(s), cyclic hydrocarbyl group with or without substituent(s), heterocyclic hydrocarbyl group with or without substituent(s) and $C_{1-6}$ acyl group with or without substituent(s);

$R_2$, $R_5$ is each independently selected from H, $OR_{33}$, $NR_{34}R_{35}$, cyano, halogen, $C_{1-8}$ hydrocarbyl group with or without substituent(s), cyclic hydrocarbyl group with or without substituent(s), heterocyclic hydrocarbyl group with or without substituent(s), $C_{1-6}$ acyl group with or without substituent(s) and amido group with or without substituent(s); wherein $R_{33}$, $R_{34}$, $R_{35}$ is each independently selected from H, $C_{1-8}$ hydrocarbyl group with or without substituent(s), cyclic hydrocarbyl group with or without substituent(s), and heterocyclic hydrocarbyl group with or without substituent(s);

$R_3$, $R_6$, $R_7$, $R_8$, $R_9$, $R_{10}$, $R_{11}$ is each independently selected from H, $OR_{27}$, $NR_{28}R_{29}$, cyano, halogen, nitro, $C_{1-8}$ hydrocarbyl group with or without substituent(s), cyclic hydrocarbyl group with or without substituent(s), heterocyclic hydrocarbyl group with or without substituent(s), $X6S(=O)_kR_{30}$, $X6C(=O)R_{31}$; wherein k is 0 to 2; wherein $R_{27}$, $R_{28}$, $R_{29}$, $R_{30}$, $R_{31}$ is each independently selected from H, $C_{1-8}$ hydrocarbyl group, cyclic hydrocarbyl group and heterocyclic hydrocarbyl group with or without substituent(s); wherein X6 is missing or selected from O, S, $NR_{32}$; wherein $R_{32}$ is H, $C_{1-8}$ hydrocarbyl group with or without substituent(s), cyclic hydrocarbyl group with or without substituent(s), or heterocyclic hydrocarbyl group with or without substituent(s);

$R_4$ is selected from H, cyano, carboxyl, $C_{1-8}$ hydrocarbyl group with or without substituent(s), and hydrocarbyloxycarbonyl group with or without substituent(s);

a is an integer between 0 and 5 (such as 1, 2, 3, 4, 5);

b is an integer between 0 and 3 (such as 1, 2, 3);

c is an integer between 0 and 30 (such as 1, 2, 3, 4, 5, 6, 7, 8, 9);

d is an integer between 0 and 9 (such as 1, 2, 3, 4, 5, 6, 7, 8, 9);

e is an integer between 0 and 3 (such as 1, 2, 3);

f is an integer between 0 and 3 (such as 1, 2, 3).

In another preferred example, A is missing; W is $-X2C(=O)X3$, wherein X2 is $NR_{18}$ and X3 is missing, or X3 is $NR_{18}$ and X2 is missing; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 1 and 6; Z is $(CR_{24}R_{25})_i$, wherein $R_{24}$, $R_{25}$ is each independently selected from H, hydroxy, $C_{1-4}$ hydrocarbyl group with or without substituent(s), i is an integer between 1 and 6; c is 0.

In another preferred example, A is missing; W is missing or O; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; B is O; Z is $(CR_{24}R_{25})_i$, wherein $R_{24}$, $R_{25}$ is each independently selected from H, hydroxy, $C_{1-4}$ hydrocarbyl group with or without substituent(s), i is an integer between 1 and 3; c is an integer between 1 and 6.

In another preferred example, A is $SO_2X1$; wherein X1 is missing or selected from O and S; W is missing or O; Y is $(CR_{22}R_{23})_h$, wherein $R_{22}$ and $R_{23}$ is each independently selected from H, hydroxyl, and $C_{1-4}$ hydrocarbyl group with or without substituent(s), h is an integer between 1 and 6; Z is $(CR_{24}R_{25})_i$, wherein $R_{24}$, $R_{25}$ is each independently selected from H, hydroxy, and $C_{1-4}$ hydrocarbyl group with or without substituent(s), i is an integer between 0 and 3; c is 0.

In another preferred example, A is missing; W is $NR_{17}$; wherein $R_{17}$ is H, or $C_{1-4}$ hydrocarbyl group with or without substituent(s); Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; Z is $(CR_{24}R_{25})_i$, wherein $R_{24}$, $R_{25}$ is each independently selected from H, hydroxy, and $C_{1-4}$ hydrocarbyl group with or without substituent(s), i is an integer between 1 and 4; B is O; c is an integer between 1 and 6.

In another preferred example, A is missing; W is missing; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; Z is $(CR_{24}R_{25})_i$, wherein $R_{24}$, $R_{25}$ is each independently selected from H, hydroxy, and $C_{1-4}$ hydrocarbyl group with or without substituent(s), i is an integer between 0 and 3; B is O; c is an integer between 1 and 10 (preferably between 1 and 6).

In another preferred example, A is $C(=O)X1-$, wherein X1 is missing or selected from a 3- to 8-membered heteroaromatic ring (preferably such as a pyridine ring or a 1,2,3-triazole ring) with or without substituent(s), and 3- to 8-membered aromatic rings (preferably a benzene ring) with or without substituent(s).

In another preferred example, A is C(=O) and Y is C(=CH2)(CR₂₂R₂₃)ₕ, wherein h is an integer between 0 and 10 (preferably an integer between 0 and 5).

In another preferred example, any of the substituents is selected from the group consisting of halogen, unsubstituted or halogenated C1-C6 alkyl, unsubstituted or halogenated C1-C6 alkoxy, unsubstituted or halogenated C2-C6 alkoxyalkyl, unsubstituted or halogenated C3-C8 cycloalkyl, unsubstituted or halogenated C2-C6 alkylcarbonyl, unsubstituted or halogenated C1-C6 alkylene-hydroxyl, unsubstituted or C1-C6 alkyl substituted amine.

In another preferred example, the structure of the compound is represented by formula I':

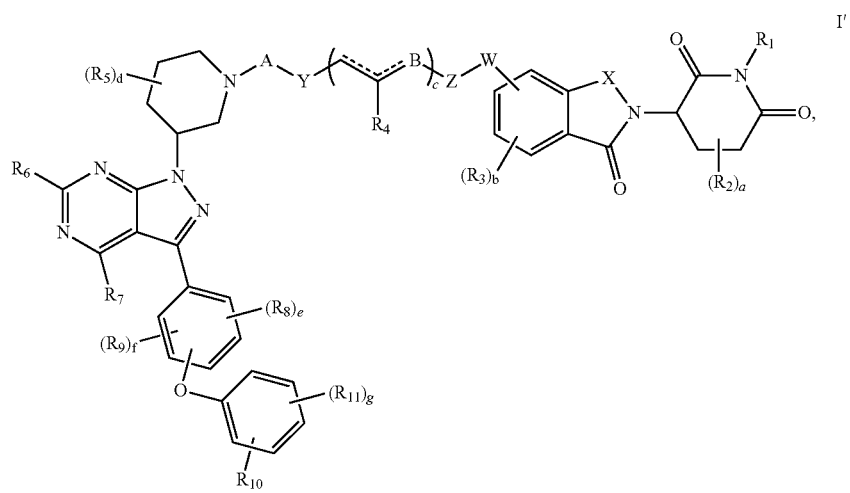

wherein, each group is defined as described above.

In another preferred example, the structure of the compound is represented by formula I":

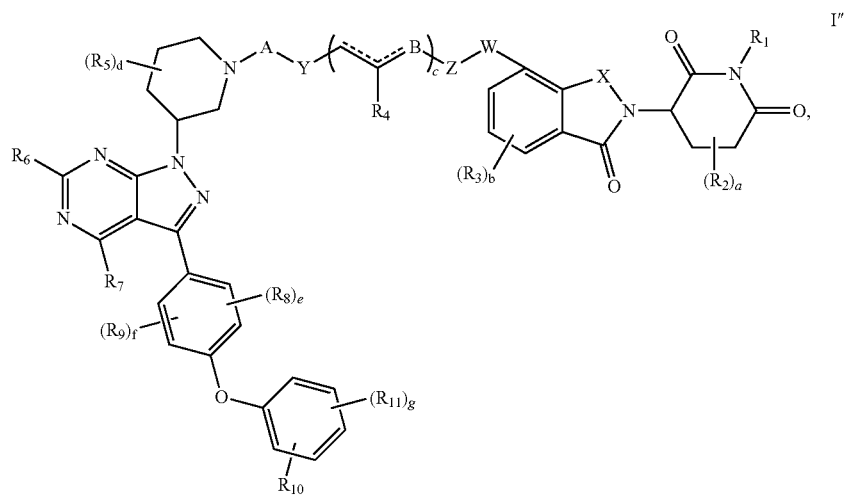

wherein, each group is defined as described above.

In another preferred example, the structure of the compound is represented by formula II":

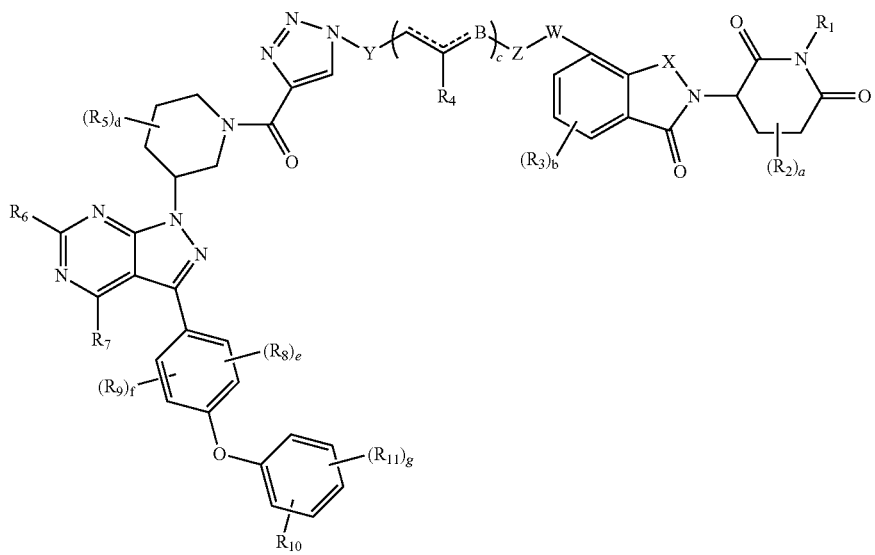

wherein, each group is defined as described above.

In another preferred example, in formula I, I', I", or I'", ------- represents a single bond.

In another preferred example, X is C(=O).

In another preferred example, $R_1$ is selected from H and $C_{1-4}$ alkyl with or without substituent(s).

In another preferred example, $R_2$, $R_5$ is each independently selected from H and $C_{1-4}$ alkyl with or without substituent(s).

In another preferred example, $R_3$ is selected from H and $C_{1-4}$ alkyl with or without substituent(s).

In another preferred example, $R_6$ is selected from H, $C_{1-4}$ alkyl with or without substituent(s), and $OR_{29}$; wherein $R_{29}$ is selected from H and $C_{1-6}$ alkyl with or without substituent(s).

In another preferred example, $R_7$ is selected from H, $C_{1-4}$ alkyl with or without substituent(s), and $NR_{28}R_{29}$; wherein $R_{28}$, $R_{29}$ is each independently selected from H and $C_{1-4}$ hydrocarbyl group with or without substituent(s).

In another preferred example, $R_8$ is selected from H, halogen and $C_{1-4}$ alkyl with or without substituent(s).

In another preferred example, $R_9$ is selected from H, halogen and $C_{1-4}$ alkyl with or without substituent(s).

In another preferred example, $R_{10}$ is selected from H, halogen, cyano, nitro, and $C_{1-4}$ alkyl with or without substituent(s).

In another preferred example, $R_{11}$ is selected from H, halogen, cyano, nitro, and $C_{1-4}$ alkyl with or without substituent(s).

In another preferred example, $R_4$ is selected from H, cyano and $C_{1-6}$ alkyl with or without substituent(s).

In the second aspect of the present invention, there is provided a pharmaceutical composition, which comprises the compound according to the first aspect or a pharmaceutically acceptable salt thereof, or a prodrug thereof, and a pharmaceutically acceptable carrier.

In another preferred example, the effective amount refers to a therapeutically effective amount or an inhibitory effective amount, preferably 0.01 to 99.99%.

In another preferred example, the pharmaceutical composition further comprises one or more antitumor agents.

In another preferred example, the pharmaceutical composition is used to inhibit the activity of Bruton's tyrosine kinase (Btk).

In another preferred example, the pharmaceutical composition is used for treating diseases related to the activity or expression level of Bruton's tyrosine kinase (Btk).

In the third aspect of the present invention, there is provided a use of the compound according to the first aspect of the present invention for:

(a) preparation of drugs for the treatment of diseases related to the activity or expression level of Bruton's tyrosine kinase (Btk);

(b) preparation of Bruton's tyrosine kinase (Btk) targeting inhibitors or degradation agents;

(c) non-therapeutic inhibition or degradation of the activity of Bruton's tyrosine kinase (Btk) in vitro;

(d) non-therapeutic inhibition of tumor cell proliferation in vitro; and/or (e) treatment of diseases related to the activity or expression level of Bruton's tyrosine kinase (Btk).

In another preferred example, the diseases include tumors and autoimmune diseases; preferably, the tumors include non-Hodgkin's lymphoma (NHL), chronic lymphocytic leukemia (CLL), B-cell lymphoma, etc.; the autoimmune diseases include rheumatoid arthritis, psoriasis, etc.

In the fourth aspect of the present invention, there is provided a method for preparing the compound of formula I according to the first aspect of the present invention, comprising the step of:

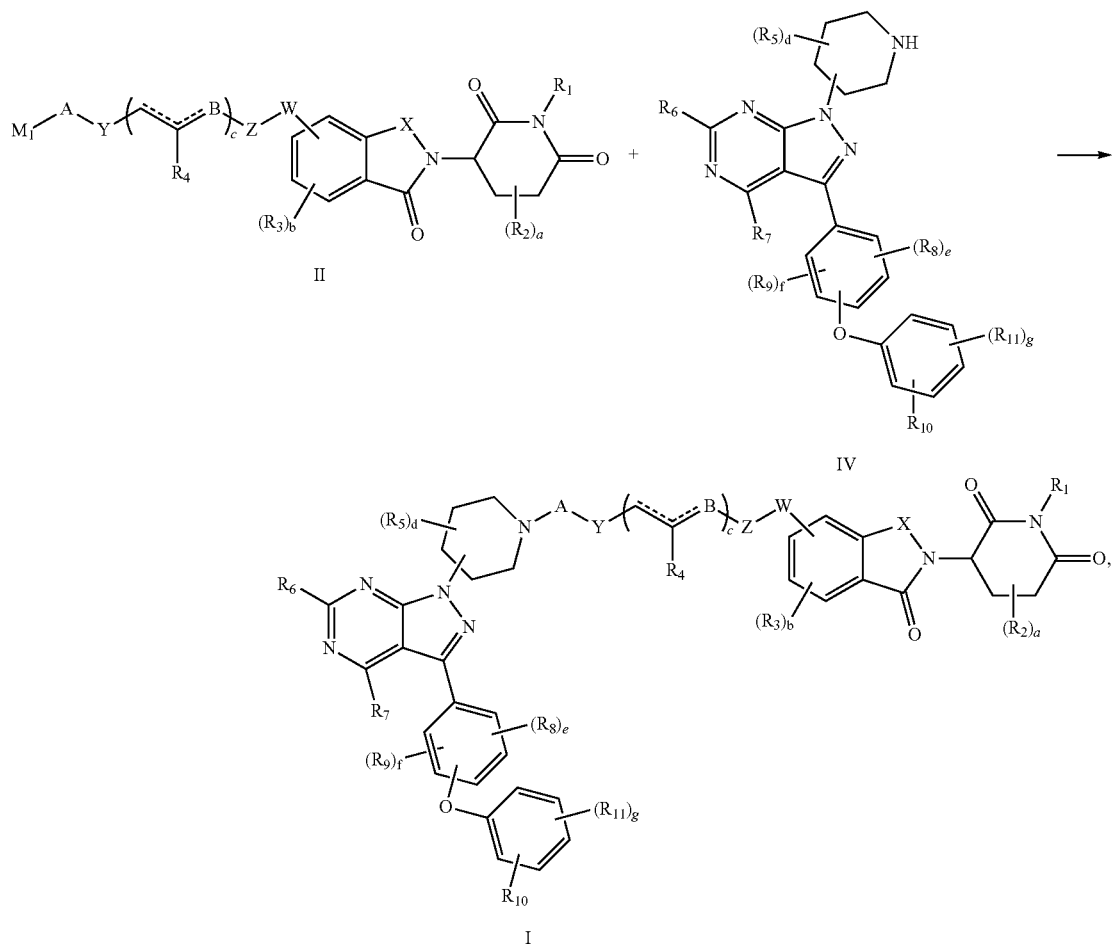

(a) reacting a compound of formula IV and a compound of formula II in an inert solvent to obtain a compound of formula I;

in the above formulas, the definition of each group is as described above, and $M_1$ is a leaving group.

In another preferred example, the method further comprises the step of:

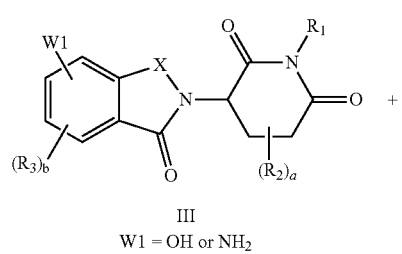

III
W1 = OH or NH$_2$

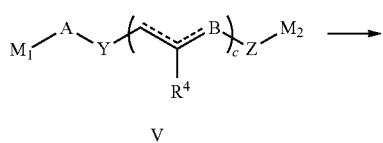

V

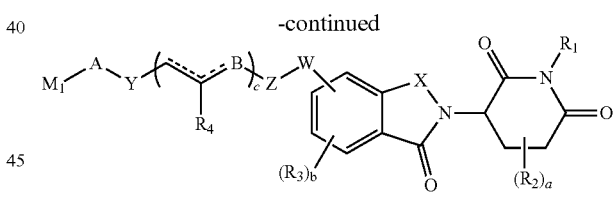

II (b) reacting a compound of formula III and a compound of formula V in an inert solvent to obtain a compound of formula II; $M_1$ and $M_2$ are leaving groups.

In the fifth aspect of the present invention, there is provided a method for inhibiting or degrading the activity of Bruton's tyrosine kinase (Btk), comprising the step of administering an inhibitory effective amount of the compound of formula I or a pharmaceutically acceptable salt thereof according to the first aspect of the present invention to an inhibitory subject, or administering an inhibitory effective amount of the pharmaceutical composition according to the fourth aspect of the present invention to an inhibitory subject.

In another preferred example, the inhibition is non-therapeutic inhibition in vitro.

In another preferred example, when an inhibitory effective amount of the compound of formula I or a pharmaceutically acceptable salt thereof according to the first aspect of the present invention is administered to an inhibitory subject, the inhibitory effective amount is 0.001-500 nmol/L, preferably 0.01-200 nmol/L.

In the sixth aspect of the present invention, there is provided a method for treating a disease related to the activity or expression level of Bruton's tyrosine kinase (Btk), comprising a step of: administering a therapeutically effective amount of the compound of formula I according to the first aspect of the present invention or the pharmaceutical composition according to the fourth aspect of the present invention to a treating subject.

In another preferred example, the subject is a mammal; preferably, the mammal is a human.

In another preferred example, the disease related to the activity or expression level of Bruton's tyrosine kinase (Btk) is a tumor or an autoimmune disease.

In the seventh aspect of the present invention, there is provided a method for inhibiting tumor cells in vitro, the method comprising: administering an inhibitory effective amount of the compound of formula I according to the first aspect of the present invention or the pharmaceutical composition according to the second aspect of the present invention to an inhibitory subject.

It is to be understood that within the scope of the present invention, the various technical features of the present invention and the various technical features specifically described hereinafter (as in the embodiments) may be combined with each other to form a new or preferred technical solution. Due to space limitations, we will not repeat them here.

DETAILED DESCRIPTION OF THE INVENTION

After extensive and intensive research, the present inventors have prepared a class of compounds having the structure shown in formula I and have found that they have inhibitory and degradation activities on Bruton's tyrosine kinase (Btk). In addition, the compound has an inhibitory effect on Bruton's tyrosine kinase (Btk) at a very low concentration, and the inhibitory activity is quite excellent, so it can be used for the treatment of diseases related to the activity or expression level of Bruton's tyrosine kinase (Btk), such as tumors. The present invention has been completed on this basis.

The present invention has disclosed a new class of compounds and its use for inhibiting and degrading Bruton's tyrosine kinase (Btk). These compounds can inhibit and degrade Btk and be used to treat tumors or autoimmune diseases.

Term

In the present invention, the term "$C_{1-8}$ hydrocarbyl group" refers to a functional group containing only two kinds of atoms of carbon and hydrogen, in which the number of carbon atoms is 1 to 8. A hydrocarbyl group can be regarded as a free radical left after the corresponding hydrocarbon loses one hydrogen atom, which may be an alkyl group, a cycloalkyl group, an alkenyl group, or an alkynyl group, etc.; it may be linear, branched, or cyclic; and it is aliphatic or aromatic.

The term "$C_{1-6}$ alkyl" refers to a straight or branched alkyl group having 1 to 6 carbon atoms, such as methyl, ethyl, propyl, isopropyl, butyl, isobutyl, sec-butyl, tert-butyl, or similar groups.

The term "alkoxy" as used herein includes O-alkyl, in which "alkyl" is as defined above.

The term "halogenated" as used herein, unless otherwise indicated, includes fluoro, chloro, bromo or iodo.

The compound of the present invention may contain a double bond. When such double bond is contained, the compounds of the present invention exist in cis form, trans form or mixtures thereof.

The halogens described herein include fluorine, chlorine, bromine and iodine.

Unless otherwise indicated, the alkyl and the alkyl moieties of the alkoxy group herein may be linear, branched, or cyclic.

In the present invention, the term "cyclic hydrocarbyl group" refers to a functional group containing two kind of atoms of carbon and hydrogen, and includes cycloalkyl, cycloalkenyl (containing at least one carbon-carbon double bond), and aryl. They can be monocyclic, bicyclic, and polycyclic. They can be spiro rings or fused rings.

In the present invention, the term "heterocyclic hydrocarbyl group" refers to a functional group containing carbon, hydrogen, and at least one heteroatom other than carbon and hydrogen. It includes heterocycloalkyl, heterocycloalkenyl (containing at least one carbon-carbon double bond), and heteroaryl. One or more ring-forming atoms in the ring are heteroatoms. The heteroatoms can be O, N, S, or any combination thereof. They can be monocyclic, bicyclic or polycyclic. They can be spiro rings or fused rings.

In the present invention, the term "substituent" includes, but is not limited to, fluorine, chlorine, bromine, cyano, hydroxyl, amino, $C_{1-6}$ hydrocarbyloxy group, $C_{1-6}$ halohydrocarbyl group, $C_{1-6}$ acyl group, $C_{1-6}$ sulfonyl group.

The term "hydrocarbyloxy group" as used herein refers to an O-hydrocarbyl group, where the "hydrocarbyl group" is as defined above.

The term "hydrocarbyloxycarbonyl group" as used herein refers to a C(=O)O-hydrocarbyl group, in which the "hydrocarbyl group" is as defined above.

The term "amino" as used herein refers to N(H or hydrocarbyl 1) (H or hydrocarbyl 2), in which the "hydrocarbyl group" is as defined above.

The term "aminocarbonyl group" as used herein refers to a C(=O)-amino group, in which the "amino" is as defined above.

The term "amido" as used herein refers to N(H or hydrocarbyl group)-C(=O)-hydrocarbyl group, in which the "hydrocarbyl group" is as defined above.

In the present invention, the term "containing", "comprising" or "including" means that various ingredients can be used together in the mixture or composition of the present invention. Thus, the terms "consisting essentially of" and "consisting of" are included in the term "containing".

In the present invention, the term "pharmaceutically acceptable" ingredient refers to a substance suitable for human and/or animals without excessive adverse side effects (such as toxicity, irritation and allergy), that is, with a reasonable benefit/risk ratio.

In the present invention, the term "effective amount" refers to an amount of a therapeutic agent to treat, alleviate or prevent a target disease or condition, or an amount that exhibits a detectable therapeutic or preventive effect. The exact effective amount for a subject will depend on the subject's size and health, the nature and extent of the condition, and the therapeutic agent and/or combination of therapeutic agents chosen for administration. Therefore, it is not useful to specify an accurate effective amount in advance. However, for a given condition, routine experimentation can be used to determine the effective amount, which the clinician can determine.

As used herein, unless specifically stated, the term "substituted" refers to the replacement of one or more hydrogen atoms on a group with a substituent selected from the group consisting of: halogen, unsubstituted or halogenated $C_{1-6}$ alkyl, unsubstituted or halogenated $C_{2-6}$ acyl, unsubstituted or halogenated $C_{1-6}$ alkyl-hydroxy.

Unless otherwise specified, all compounds present in the present invention are intended to include all possible optical isomers, such as a single chiral compound, or a mixture of various chiral compounds (ie, a racemate). Among all the compounds of the present invention, each chiral carbon atom may optionally be in the R configuration or the S configuration, or a mixture of the R configuration and the S configuration.

As used herein, the term "the compound of the present invention" refers to a compound of formula I. The term also includes various crystalline forms, pharmaceutically acceptable salts, hydrates or solvates of the compound of formula I.

As used herein, the term "pharmaceutically acceptable salt" refers to a salt of the compound of the present invention with an acid or base suitable for use as a medicament. The pharmaceutically acceptable salts include inorganic and organic salts. One preferred class of salts is salts of the compound of the present invention with an acid. Suitable acids for forming salts include, but are not limited to, inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzylsulfonic acid, benzenesulfonic acid etc.; and acidic amino acids such as aspartic acid, glutamic acid etc.

Compounds and Pharmaceutically Acceptable Salts Thereof

The present invention relates to a compound of formula I shown as below or a pharmaceutically acceptable salt thereof;

substituent(s); wherein X1 is missing or selected from $(CR_{12}R_{13})_jO$, $(CR_{12}R_{13})_j$, 3- to 8-membered heteroaromatic ring (preferably, such as pyridyl, or 1,2,3-triazolyl) with or without substituent(s), 3- to 8-membered aromatic ring (preferably, such as phenyl) with or without substituent(s), and $NR_{14}$; wherein $R_{14}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

W is missing or selected from O, $NR_{17}$, $-X2C(=O)X3$, $-X2S(=O)_gX3$; wherein $R_{17}$ is independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); wherein X2, X3 is each independently missing or selected from O, S, and $NR_{18}$; wherein g is an integer between 0 and 2; wherein R18 is independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Y is $(CR_{22}R_{23})_h$, $CHX4(CR_{22}R_{23})_h$, $CX4=CH(CR_{22}R_{23})_h$, or $(CR_{22}R_{23})_h$; wherein h is an integer between 0 and 30; wherein $R_{22}$, $R_{23}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X4 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

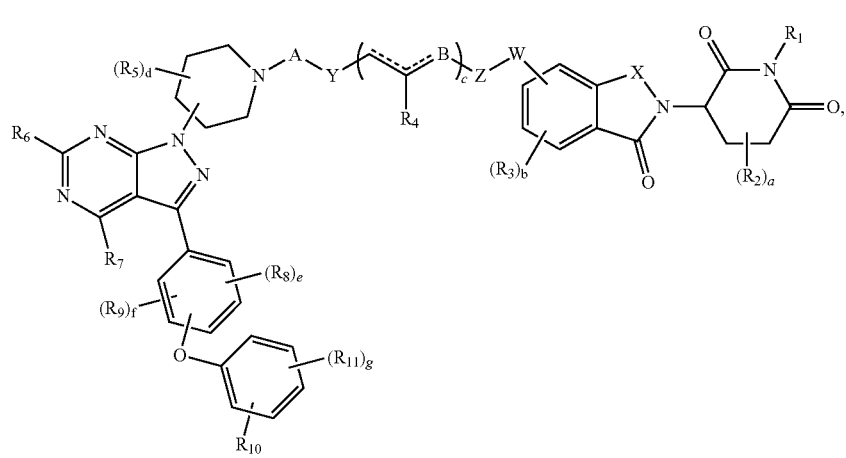

wherein,
— refers to a single bond;
------- to a single or double bond; A is missing or selected from $C(=O)$, $C(=O)X1-$, $SOX1-$, $SO_2X1-$, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without Z is $(CR_{24}R_{25})_i$, $CHX5(CR_{24}R_{25})_i$, $CX5=CH(CR_{24}R_{25})_i$ or $C\equiv C(CR_{24}R_{25})_i$; wherein i is an integer between 0 and 30; wherein $R_{24}$, $R_{25}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X5 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

B is missing or selected from O, C=O, S, $NR_{15}$, $-NR_{15}C(=O)-$, $-C(=O)NR_{15}-$, $-C(=O)O-$, $OC(=O)O-$, $-NR_{15}C(=O)O-$, $-OC(=O)NR_{15}-$, $-NR_{15}C(=O)NR_{16}-$, $C_{1-12}$ hydrocarbyl group with or without substituent(s), $C_{1-12}$ cyclic hydrocarbyl group with or without substituent(s), and $C_{1-12}$ heterocyclic hydrocarbyl group with or without substituent(s); wherein $R_{15}$, $R_{16}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

X is selected from $CR_{19}R_{20}$, $C(=O)$, $S(=O)$, $SO_2$, $NR_{21}$; wherein $R_{19}$, $R_{20}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein $R_{21}$ is selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_1$ is selected from H, $C_{1-8}$ hydrocarbyl group with or without substituent(s), cyclic hydrocarbyl group with or without substituent(s), heterocyclic hydrocarbyl group with or without substituent(s) and $C_{1-6}$ acyl group with or without substituent(s);

$R_2$, $R_5$ is each independently selected from H, $OR_{33}$, $NR_{34}R_{35}$, cyano, halogen, $C_{1-8}$ hydrocarbyl group with or without substituent(s), cyclic hydrocarbyl group with or without substituent(s), heterocyclic hydrocarbyl group with or without substituent(s), $C_{1-6}$ acyl group with or without substituent(s) and amido group with or without substituent(s); wherein $R_{33}$, $R_{34}$, $R_{35}$ is each independently selected from H, $C_{1-8}$ hydrocarbyl group with or without substituent(s), cyclic hydrocarbyl group with or without substituent(s), and heterocyclic hydrocarbyl group with or without substituent(s);

$R_3$, $R_6$, $R_7$, $R_8$, $R_9$, $R_{10}$, $R_{11}$ is each independently selected from H, $OR_{27}$, $NR_{28}R_{29}$, cyano, halogen, nitro, $C_{1-8}$ hydrocarbyl group with or without substituent(s), cyclic hydrocarbyl group with or without substituent(s), heterocyclic hydrocarbyl group with or without substituent(s), $X6S(=O)_kR_{30}$, $X6C(=O)R_{31}$; wherein k is 0 to 2; wherein $R_{27}$, $R_{28}$, $R_{29}$, $R_{30}$, $R_{31}$ is each independently selected from H, $C_{1-8}$ hydrocarbyl group, cyclic hydrocarbyl group and heterocyclic hydrocarbyl group with or without substituent(s); wherein X6 is missing or selected from O, S, $NR_{32}$; wherein $R_{32}$ is H, $C_{1-8}$ hydrocarbyl group with or without substituent(s), cyclic hydrocarbyl group with or without substituent(s), and heterocyclic hydrocarbyl group with or without substituent(s);

$R_4$ is selected from H, cyano, carboxyl, $C_{1-8}$ hydrocarbyl group with or without substituent(s), and hydrocarbyloxycarbonyl group with or without substituent(s);

a is an integer between 0 and 5 (such as 1, 2, 3, 4, 5);

b is an integer between 0 and 3 (such as 1, 2, 3);

c is an integer between 0 and 30 (such as 1, 2, 3, 4, 5, 6, 7, 8, 9);

d is an integer between 0 and 9 (such as 1, 2, 3, 4, 5, 6, 7, 8, 9);

e is an integer between 0 and 3 (such as 1, 2, 3);

f is an integer between 0 and 3 (such as 1, 2, 3).

Unless otherwise specified, the integer described herein is 0, 1, 2, 3, 4, 5, 6, 7, 8, or 9. In another preferred example, each of the $C_{1-8}$ cyclic hydrocarbyl groups is preferably a $C_{3-8}$ cyclic hydrocarbyl group (such as a $C_{3-8}$ cycloalkyl).

In another preferred example, each $C_{1-8}$ heterocyclic hydrocarbyl group is preferably a $C_{3-8}$ heterocyclic hydrocarbyl group (such as a 4- to 10-membered heterocycloalkyl group having 3-8 carbon atoms).

In a preferred embodiment of the present invention, the compound is selected from the following group consisting of:

| Compound No. | Structure |
|---|---|
| 3 | 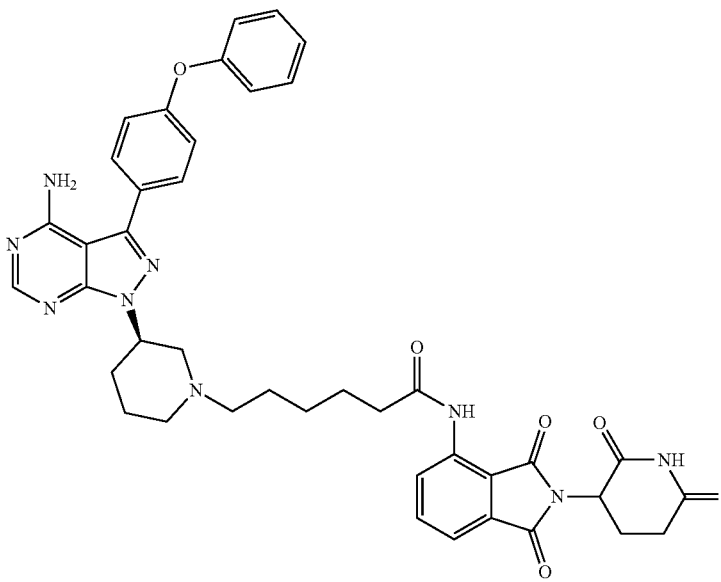 |

-continued
| Compound No. | Structure |
|---|---|
| 7 | 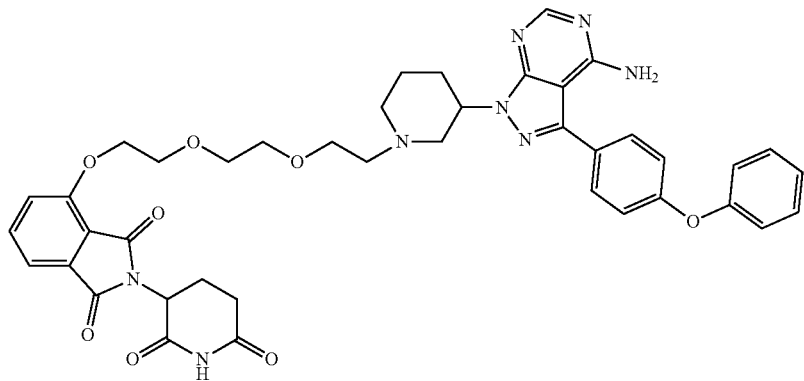 [SMILES: Nc1ncnc2c1c(-c1ccc(Oc3ccccc3)cc1)nn2C1CCCN(CCOCCOCCOc2cccc3c2C(=O)N(C2CCC(=O)NC2=O)C3=O)C1] |
| 10 | 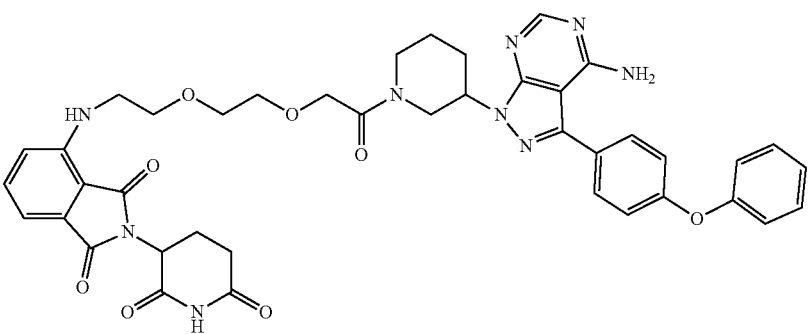 [SMILES: Nc1ncnc2c1c(-c1ccc(Oc3ccccc3)cc1)nn2C1CCCN(C(=O)COCCOCCNc2cccc3c2C(=O)N(C2CCC(=O)NC2=O)C3=O)C1] |
| 13 | 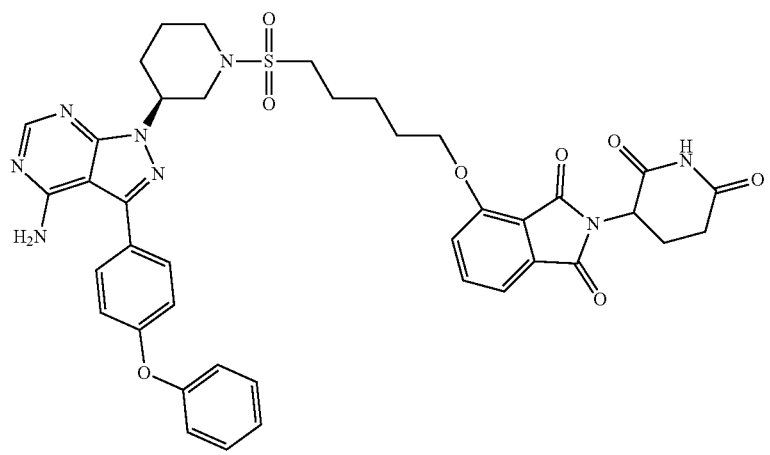 [SMILES: Nc1ncnc2c1c(-c1ccc(Oc3ccccc3)cc1)nn2[C@H]1CCCN(S(=O)(=O)CCCCCOc2cccc3c2C(=O)N(C2CCC(=O)NC2=O)C3=O)C1] |
| 14 | 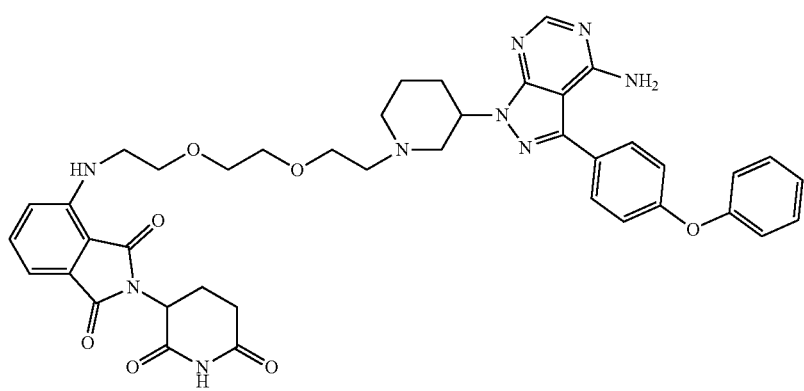 [SMILES: Nc1ncnc2c1c(-c1ccc(Oc3ccccc3)cc1)nn2C1CCCN(CCOCCOCCNc2cccc3c2C(=O)N(C2CCC(=O)NC2=O)C3=O)C1] |

| Compound No. | Structure |
|---|---|
| 15 | 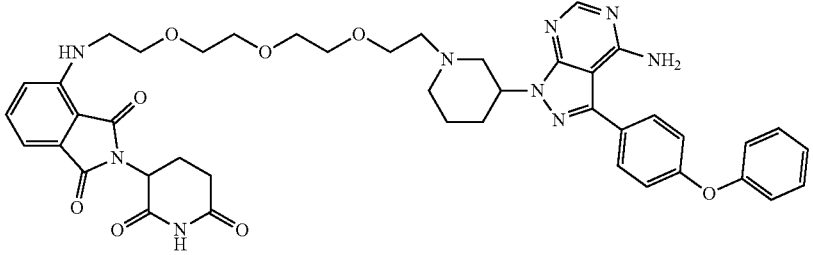 [SMILES: Nc1ncnc2c1c(-c1ccc(Oc3ccccc3)cc1)nn2C1CCCN(CCOCCOCCOCCNc2cccc3c2C(=O)N(C2CCC(=O)NC2=O)C3=O)C1] |
| 16 | 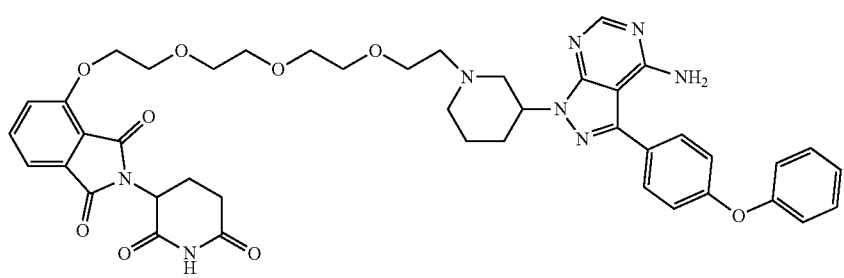 [SMILES: Nc1ncnc2c1c(-c1ccc(Oc3ccccc3)cc1)nn2C1CCCN(CCOCCOCCOCCOc2cccc3c2C(=O)N(C2CCC(=O)NC2=O)C3=O)C1] |
| 17 | 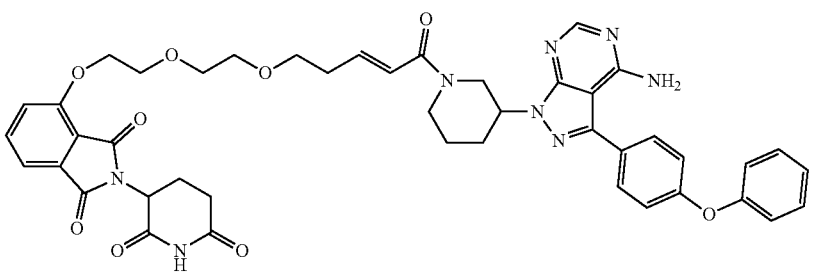 [SMILES: Nc1ncnc2c1c(-c1ccc(Oc3ccccc3)cc1)nn2C1CCCN(C(=O)/C=C/CCOCCOCCOc2cccc3c2C(=O)N(C2CCC(=O)NC2=O)C3=O)C1] |
| 18 | 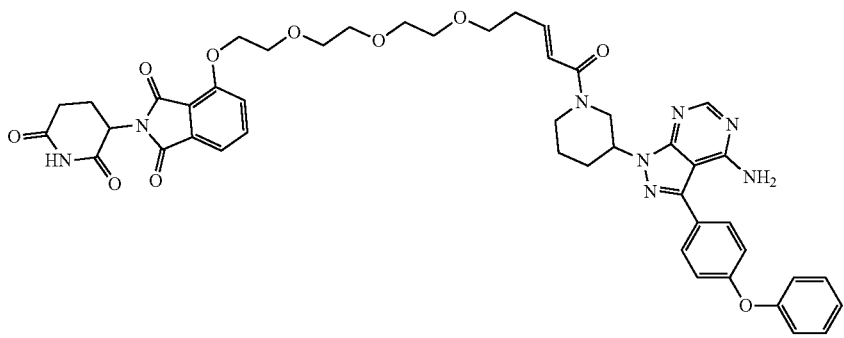 [SMILES: Nc1ncnc2c1c(-c1ccc(Oc3ccccc3)cc1)nn2C1CCCN(C(=O)/C=C/CCOCCOCCOCCOc2cccc3c2C(=O)N(C2CCC(=O)NC2=O)C3=O)C1] |

| Compound No. | Structure |
|---|---|
| 19 | 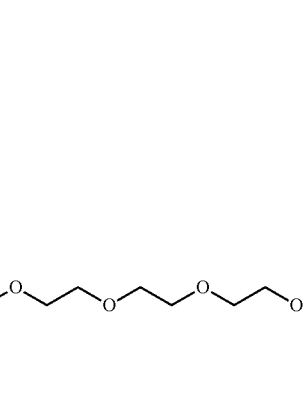 |
| 20 | 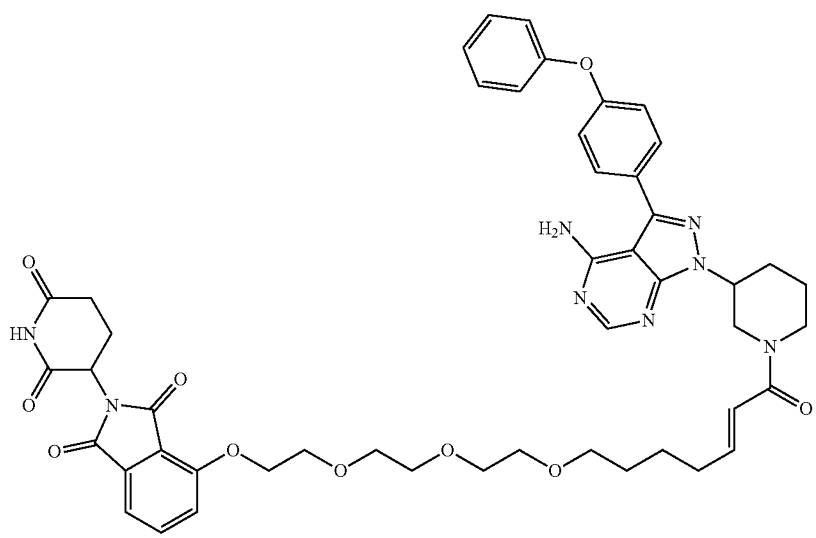 [SMILES: Nc1ncnc2c1c(-c1ccc(Oc3ccccc3)cc1)nn2C1CCCN(C(=O)/C=C/CCCCOCCOCCOCCOc2cccc3c2C(=O)N(C2CCC(=O)NC2=O)C3=O)C1] |
| 21 | 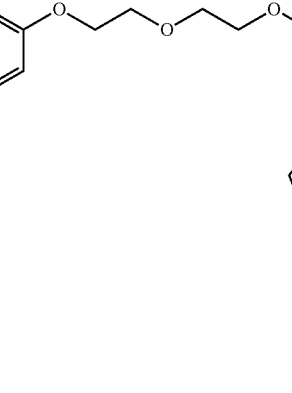 |

| Compound No. | Structure |
|---|---|
| 22 | 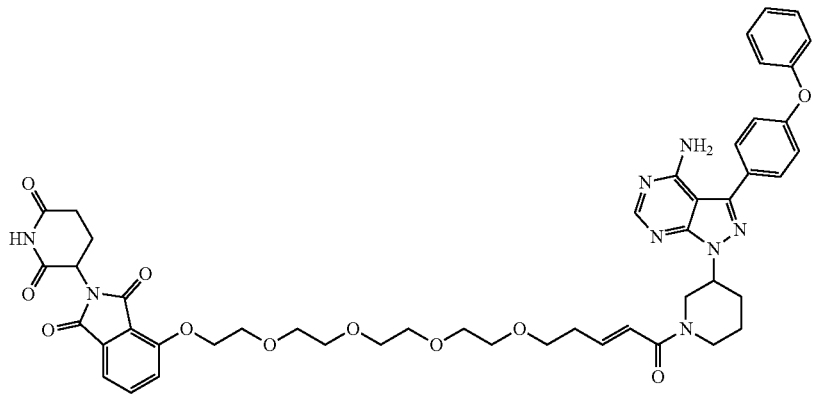 [SMILES: Nc1ncnc2c1c(-c1ccc(Oc3ccccc3)cc1)nn2C1CCCN(C(=O)/C=C/CCOCCOCCOCCOCCOc2cccc3c2C(=O)N(C2CCC(=O)NC2=O)C3=O)C1] |
| 23 | 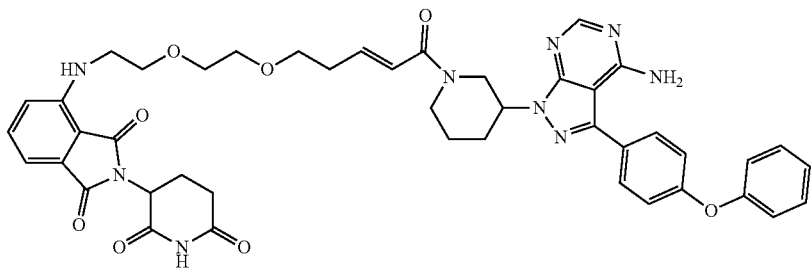 |
| 24 | 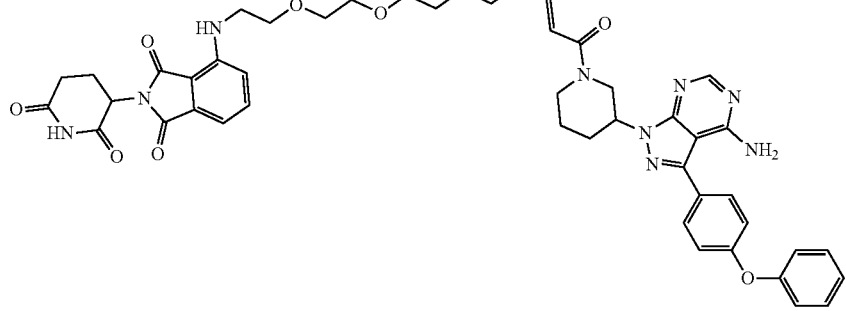 |
| 25 | 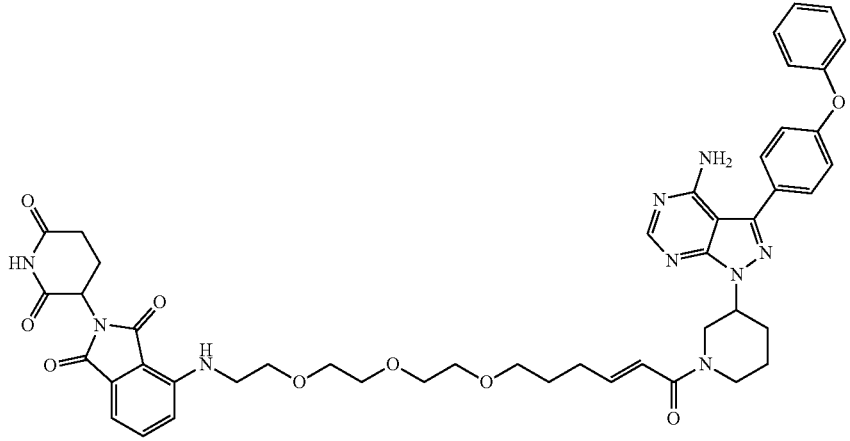 |

| Compound No. | Structure |
|---|---|
| 26 | (chemical structure) |
| 27 | (chemical structure) |
| 28 | (chemical structure) |

| Compound No. | Structure |
|---|---|
| 29 | 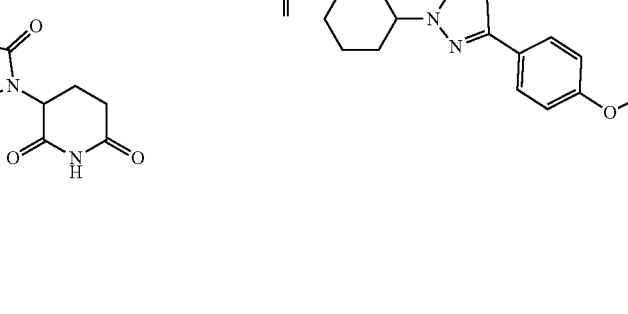 |
| 30 | 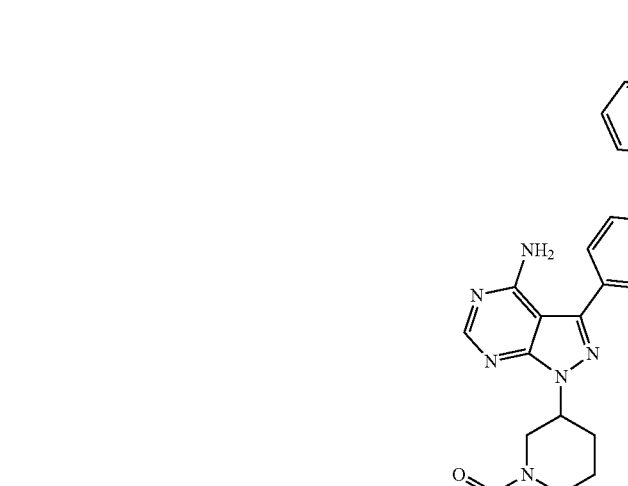 |
| 31 | 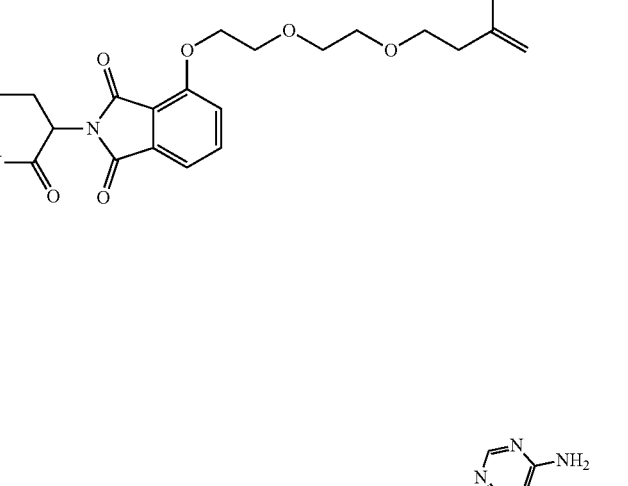 |

-continued

| Compound No. | Structure |
|---|---|
| 32 | 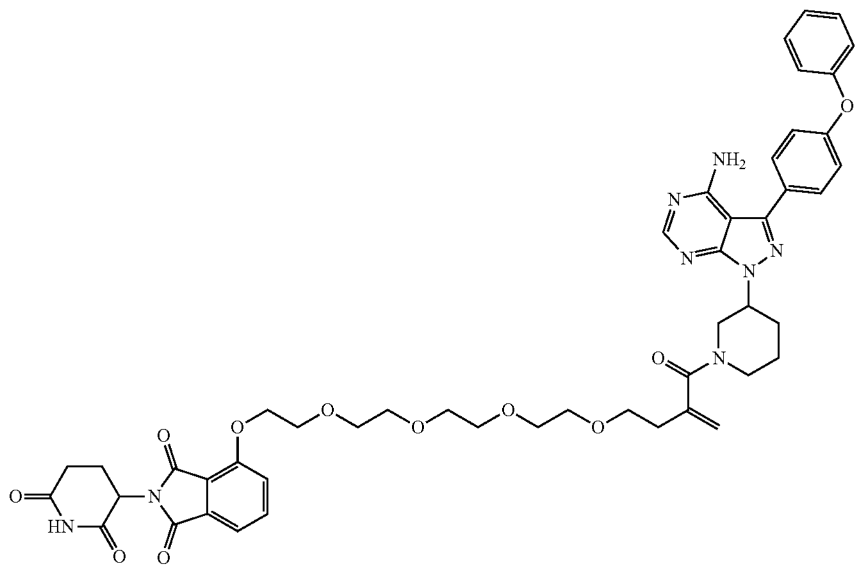 [SMILES: C=C(CCOCCOCCOCCOCCOc1cccc2c1C(=O)N(C1CCC(=O)NC1=O)C2=O)C(=O)N1CCCC(n2nc(-c3ccc(Oc4ccccc4)cc3)c3c(N)ncnc32)C1] |
| 33 | 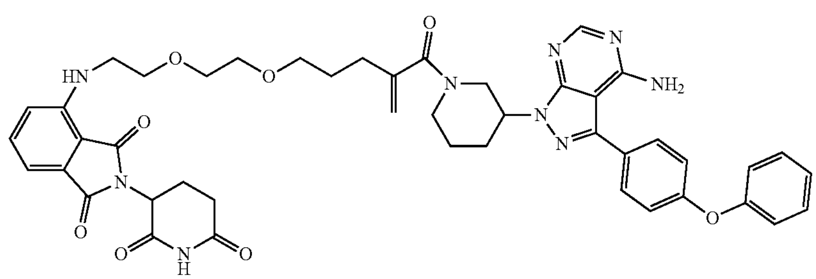 [SMILES: C=C(CCCOCCOCCNc1cccc2c1C(=O)N(C1CCC(=O)NC1=O)C2=O)C(=O)N1CCCC(n2nc(-c3ccc(Oc4ccccc4)cc3)c3c(N)ncnc32)C1] |
| 34 | 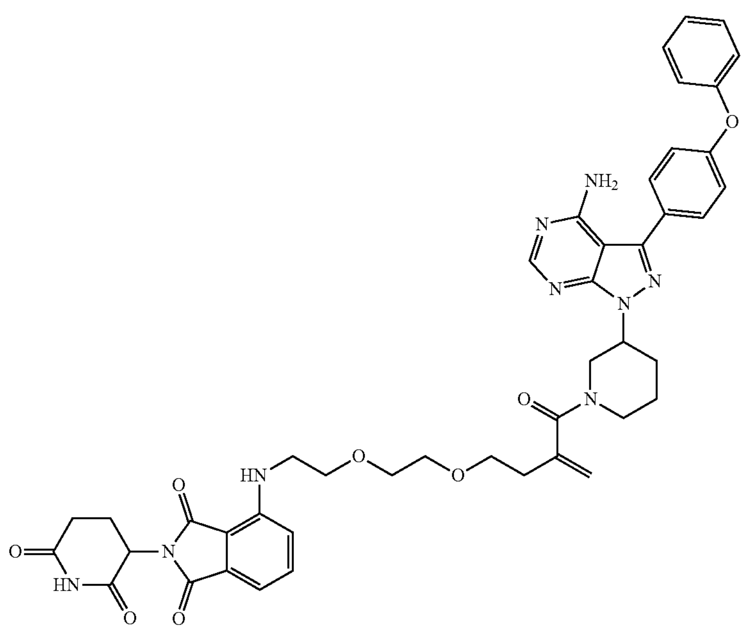 |

| Compound No. | Structure |
|---|---|
| 35 | 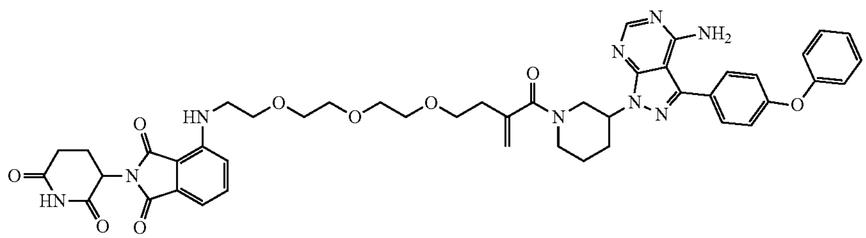 [SMILES: C=C(CCOCCOCCOCCNc1cccc2c1C(=O)N(C1CCC(=O)NC1=O)C2=O)C(=O)N1CCCC(n2nc(-c3ccc(Oc4ccccc4)cc3)c3c(N)ncnc32)C1] |
| 36 | 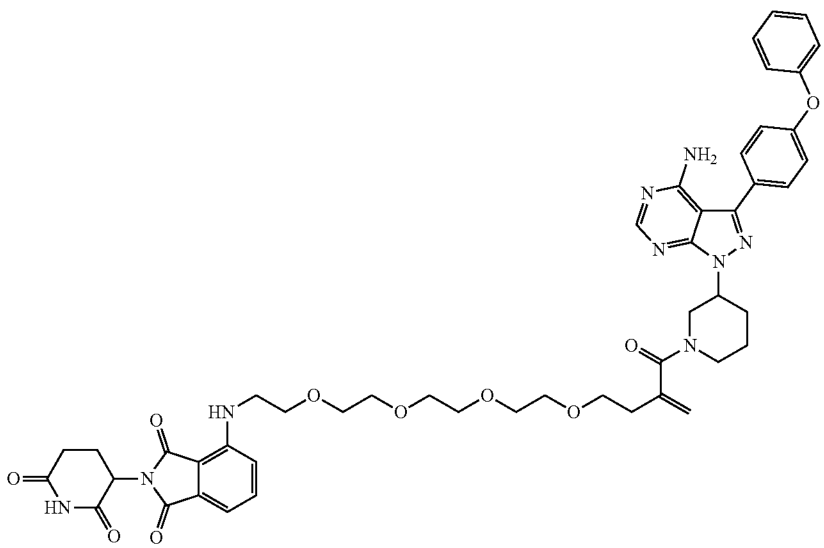 [SMILES: C=C(CCOCCOCCOCCOCCNc1cccc2c1C(=O)N(C1CCC(=O)NC1=O)C2=O)C(=O)N1CCCC(n2nc(-c3ccc(Oc4ccccc4)cc3)c3c(N)ncnc32)C1] |
| 37 | 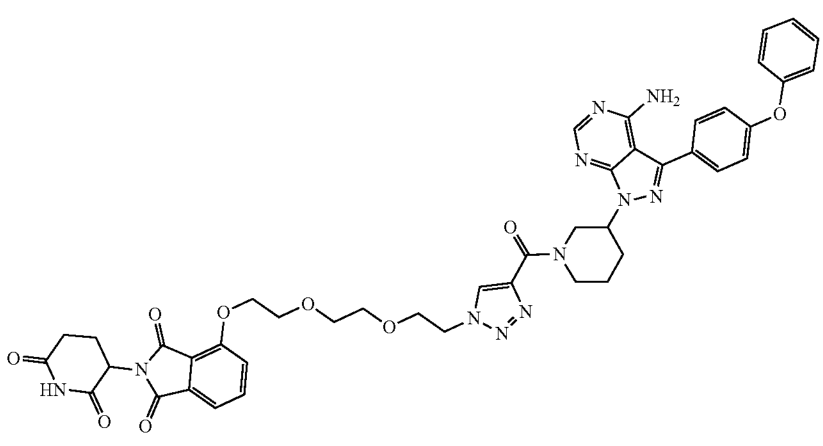 [SMILES: Nc1ncnc2c1c(-c1ccc(Oc3ccccc3)cc1)nn2C1CCCN(C(=O)c2cn(CCOCCOCCOc3cccc4c3C(=O)N(C3CCC(=O)NC3=O)C4=O)nn2)C1] |
| 39 | 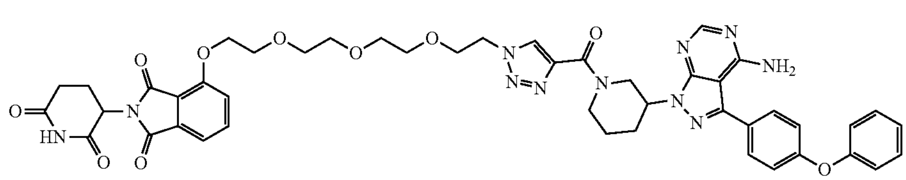 [SMILES: Nc1ncnc2c1c(-c1ccc(Oc3ccccc3)cc1)nn2C1CCCN(C(=O)c2cn(CCOCCOCCOCCOc3cccc4c3C(=O)N(C3CCC(=O)NC3=O)C4=O)nn2)C1] |

-continued

| Compound No. | Structure |
| --- | --- |
| 40 | 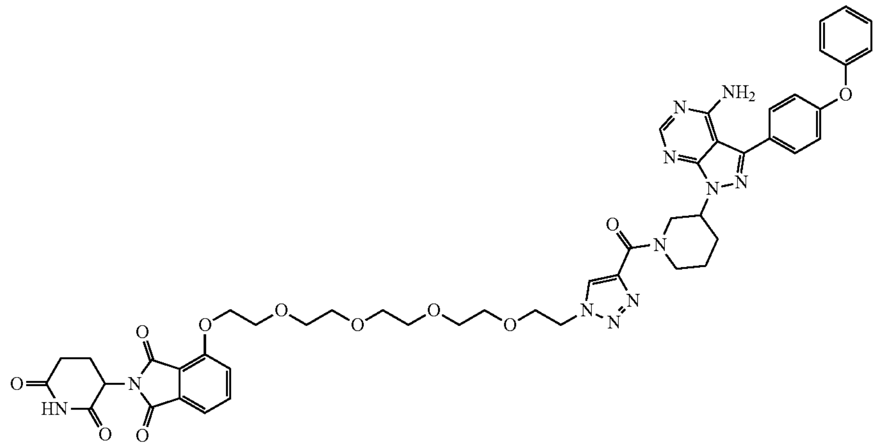 [SMILES: Nc1ncnc2c1c(-c1ccc(Oc3ccccc3)cc1)nn2C1CCCN(C(=O)c2cn(CCOCCOCCOCCOCCOc3cccc4c3C(=O)N(C3CCC(=O)NC3=O)C4=O)nn2)C1] |
| 41 | 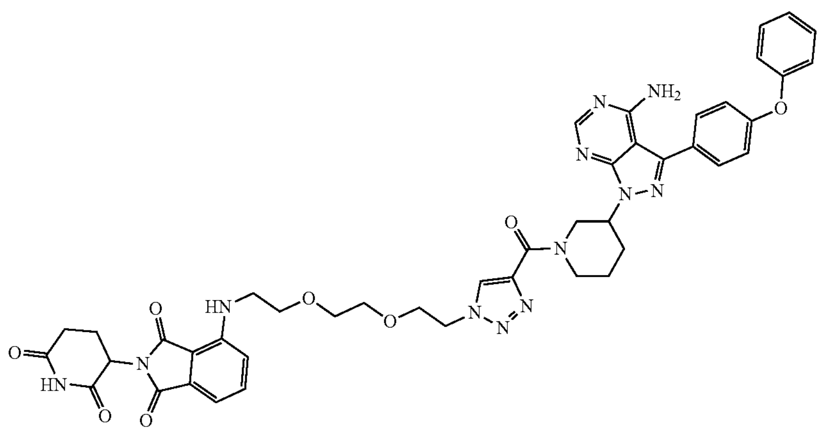 [SMILES: Nc1ncnc2c1c(-c1ccc(Oc3ccccc3)cc1)nn2C1CCCN(C(=O)c2cn(CCOCCOCCNc3cccc4c3C(=O)N(C3CCC(=O)NC3=O)C4=O)nn2)C1] |
| 43 | 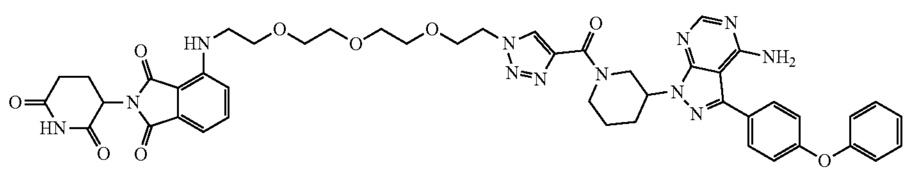 [SMILES: Nc1ncnc2c1c(-c1ccc(Oc3ccccc3)cc1)nn2C1CCCN(C(=O)c2cn(CCOCCOCCOCCNc3cccc4c3C(=O)N(C3CCC(=O)NC3=O)C4=O)nn2)C1] |
| 44 | 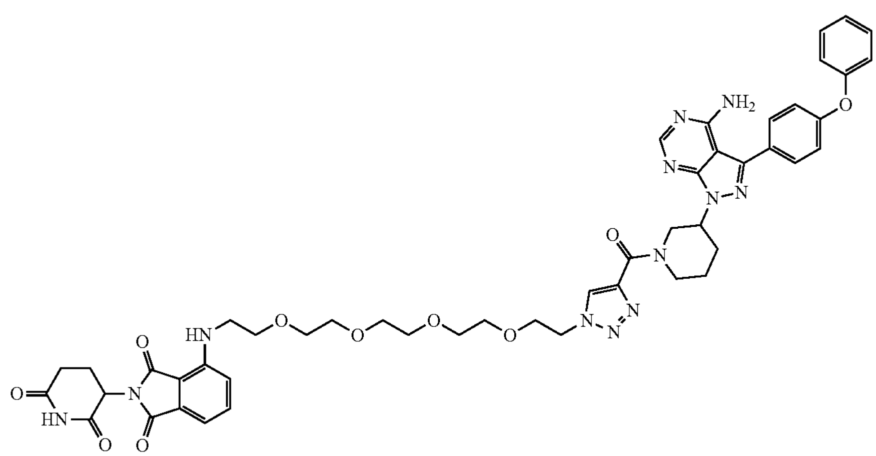 [SMILES: Nc1ncnc2c1c(-c1ccc(Oc3ccccc3)cc1)nn2C1CCCN(C(=O)c2cn(CCOCCOCCOCCOCCNc3cccc4c3C(=O)N(C3CCC(=O)NC3=O)C4=O)nn2)C1] |

The compound of the present invention may form a pharmaceutically acceptable salt with an inorganic acid, an organic acid or a base. The inorganic acid includes, but is not limited to, hydrochloric acid, hydrobromic acid, nitric acid, perchloric acid, sulfuric acid, or phosphoric acid; the organic acid includes, but is not limited to, methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, lactic acid, tartaric acid, malonic acid, glycolic acid, succinic acid, and propionic acid; the bases include, but are not limited to, inorganic salts and amines.

The term of a pharmaceutically acceptable salt refers to those salts which, according to medical judgment, are suitable for use in contact with human and mammalian tissues without excessive toxicity, irritation, allergic reactions, and the like. Pharmaceutically acceptable salts are well known in the art.

The present invention also encompasses pharmaceutical compositions containing a prodrug of a compound of formula I. Prodrugs include those compounds in which the precursor molecule is covalently bonded to the free carboxyl, hydroxyl, amino group of the compound of formula I via a carbonate bond, a urethane bond, an amide bond, an alkyl ester bond, a phosphate bond, or a phosphoramidate bond.

Preparation of Compounds
Preparation Method

The method for preparing the compound of formula I according to the present invention is described in more detail below, but these specific methods do not constitute any limitation to the present invention. The compound of the present invention can also be conveniently prepared by combining various synthetic methods described in the specification or known in the art, and such combination can be easily performed by those skilled in the art to which the present invention belongs.

The following reaction schemes illustrate the preparation of compounds of the present invention. Unless otherwise indicated, A, B, W, Y, Z, X, $M_1$, $M_2$, a, b, c, d, e, f, g, $R_1$, $R_2$, $R_3$, $R_4$, $R_5$, $R_6$, $R_7$, $R_8$, $R_9$, $R_{10}$, $R_{11}$ in the reaction scheme and subsequent discussions are as defined above.

In general, compounds of formula I can be obtained from those of formula III as described in the following schemes:

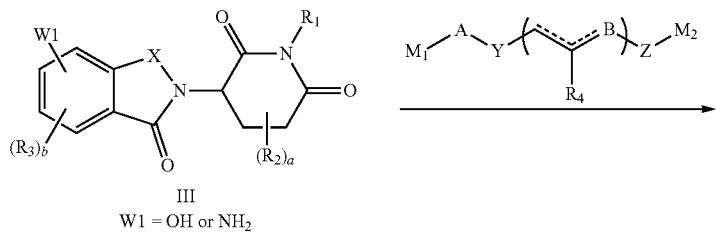

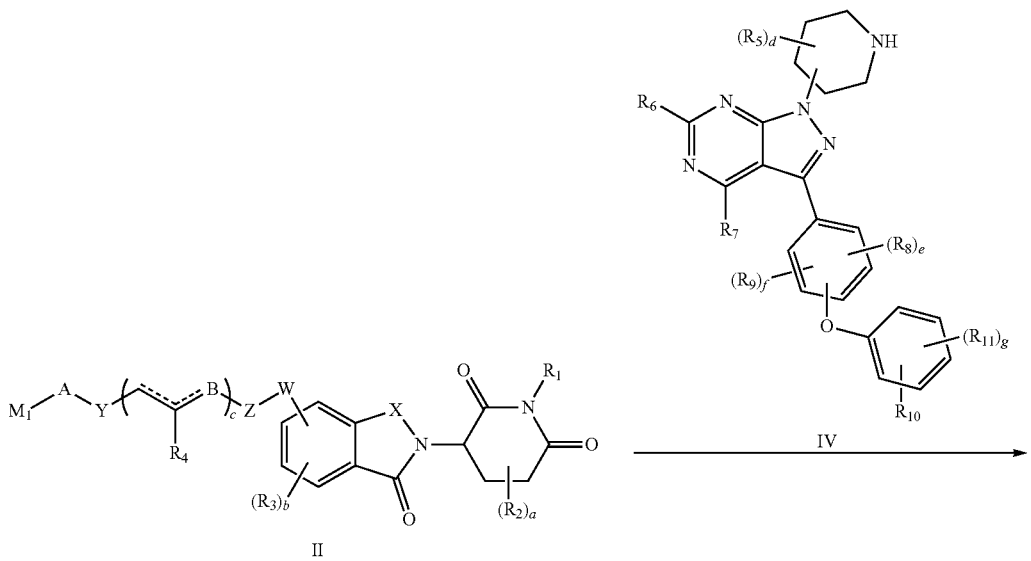

-continued

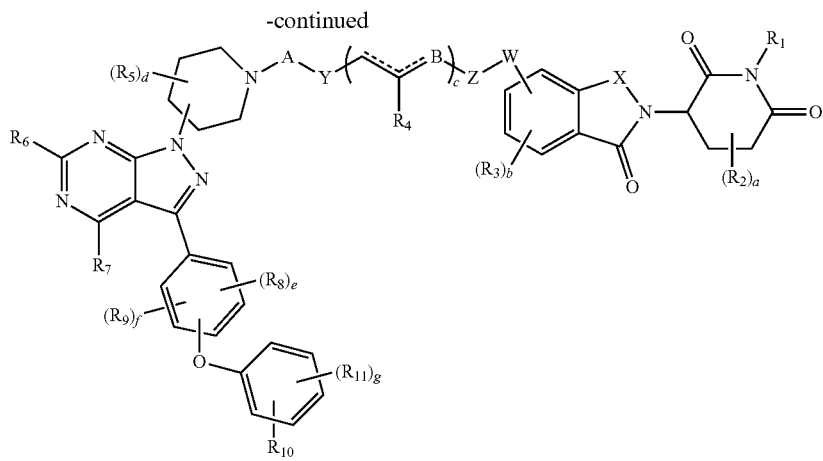

I

Compound II, in which W is an ether, can be prepared by directly nucleophilic substitution of formula III (W1=OH) with an intermediate containing a leaving group under the action of a base, or by a photo-extension reaction with an alcohol; in which W is an ester or carbamate ($NHCO_2$), it can be prepared by reacting formula III (W1=OH) with an acyl chloride, an activated ester (amide), a carboxylic acid, or an isocyanate under the action of a base; in which W is an amine, it can be prepared by directly nucleophilic substitution of formula III (W1=$NH_2$) with an intermediate containing a leaving group under the action of a base, or by reductive amination reaction of formula III (W1=$NH_2$) with an aldehyde/ketone; in which W it is an amide, alkoxycarbonylamine (OCONH) or urea, it can be prepared by reacting formula III (W1=$NH_2$) with the corresponding acyl chloride, activated ester (amide), carboxylic acid and isocyanate under the action of a base.

Compound I, in which A and a nitrogen atom are connected by a C—N bond, can be prepared by direct substitution reaction or reductive amination reaction; in which A and a nitrogen atom are connected by an amide, urea, carbamate, sulfonamide, or sulfamide form, it can be prepared by using the corresponding acyl chloride, activated ester (amide), carboxylic acid, isocyanate, sulfonyl chloride, or sulfuryl chloride.

Generally, according to the connection structure of A and W, compound I can also be obtained by first connecting formula IV with the intermediate chain and then reacting with formula III. The chemical synthesis method used is the same as described above.

Compounds of formula III or IV can be obtained by known synthetic methods or can be easily obtained commercially.

Use of Compounds of Formula I

The compound of formula I can be used for one or more of the following purposes:

(a) preparation of medicament for the treatment of diseases related to the activity or expression level of Bruton's tyrosine protein kinase (Btk);

(b) preparation of Bruton's tyrosine protein kinase (Btk) targeting inhibitors or degradation agents;

(c) non-therapeutic inhibition or degradation of the activity of Bruton's tyrosine protein kinase (Btk) in vitro;

(d) non-therapeutic inhibition of tumor cell proliferation in vitro; and/or (e) treatment of diseases related to the activity or expression level of Bruton's tyrosine protein kinase (Btk).

In another preferred example, the disease related to the activity or expression level of Bruton's tyrosine protein kinase (Btk) is a tumor, preferably a tumor selected from the group consisting of non-small cell lung cancer, inflammatory myofibroblastic tumor and so on.

The compound of formula I of the present invention can be used to prepare a pharmaceutical composition, which comprises: (i) an effective amount of a compound of formula I, or a pharmaceutically acceptable salt thereof; and (ii) a pharmaceutically acceptable carrier.

In another preferred example, the effective amount refers to a therapeutically effective amount or an inhibitory effective amount.

The compound of formula I of the present invention can also be used in a method for inhibiting or degrading Bruton's tyrosine protein kinase (Btk), and the inhibition is a non-therapeutic inhibition in vitro or a therapeutic inhibition.

In another preferred example, when an inhibitory effective amount of the compound of formula I of the present invention or a pharmaceutically acceptable salt thereof is administered to an inhibitory subject, the inhibitory effective amount is 0.001-500 nmol/L, preferably 0.01-200 nmol/L.

In particular, the present invention also provides a method of treating a disease related to the activity or expression level of Bruton's tyrosine protein kinase (Btk), and the method comprising: administering a therapeutically effective amount of a compound of formula I or a pharmaceutical composition containing the compound of formula I as an active ingredient to a subject.

Pharmaceutical Composition and Administration

Since the compound of the present invention has excellent inhibitory activity on Bruton's tyrosine kinase (Btk), the compound of the present invention and its various crystal forms, pharmaceutically acceptable inorganic or organic salts, hydrates or solvates and the pharmaceutical composition containing the compound of the present invention as a main active ingredient can be used for treating, preventing, and alleviating diseases related to Btk activity or expression level. According to the prior art, the compounds of the present invention are useful for treating diseases including tumors and the like.

The pharmaceutical composition of the present invention comprises the compound of the present invention or the pharmaceutically acceptable salts thereof in a safe and effective dosage range and pharmaceutically acceptable excipients or carriers. The "safe and effective amount" means the amount of the compound is sufficient to significantly improve the condition, but will not have serious side effects. Generally, the pharmaceutical composition contains 1-2000 mg of the compound of the present invention per dose, preferably, 2-500 mg the compound of the present invention per dose. Preferably, "one dose" is a capsule or tablet.

"Pharmaceutically acceptable carrier" means one or more compatible solid or liquid fillers or gelatinous materials which are suitable for human use and should be of sufficient purity and sufficiently low toxicity. "Compatible" herein means that each component in the composition and a compound of the present invention can be well blended with each other between them, without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (I) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent and the release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the present invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need of, in which the dose of administration is a pharmaceutically effective dose. For a person weighed 60 kg, the daily dose is usually 1-2000 mg, preferably 5-500 mg. Of course, the particular dose should also depend on various factors, such as the route of administration, the healthy condition of patient, which are well within the skills of an experienced physician.

The main advantages of the present invention include:

1. Compounds of formula I are provided.

2. A novel Btk inhibitor and preparation and application thereof are provided. The inhibitor can inhibit the activity of Btk at very low concentrations.

3. A pharmaceutical composition for treating diseases related to Btk activity is provided.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless stated otherwise, percentages and parts are percentages by weight and parts by weight.

Example 1 Preparation of Compound 3

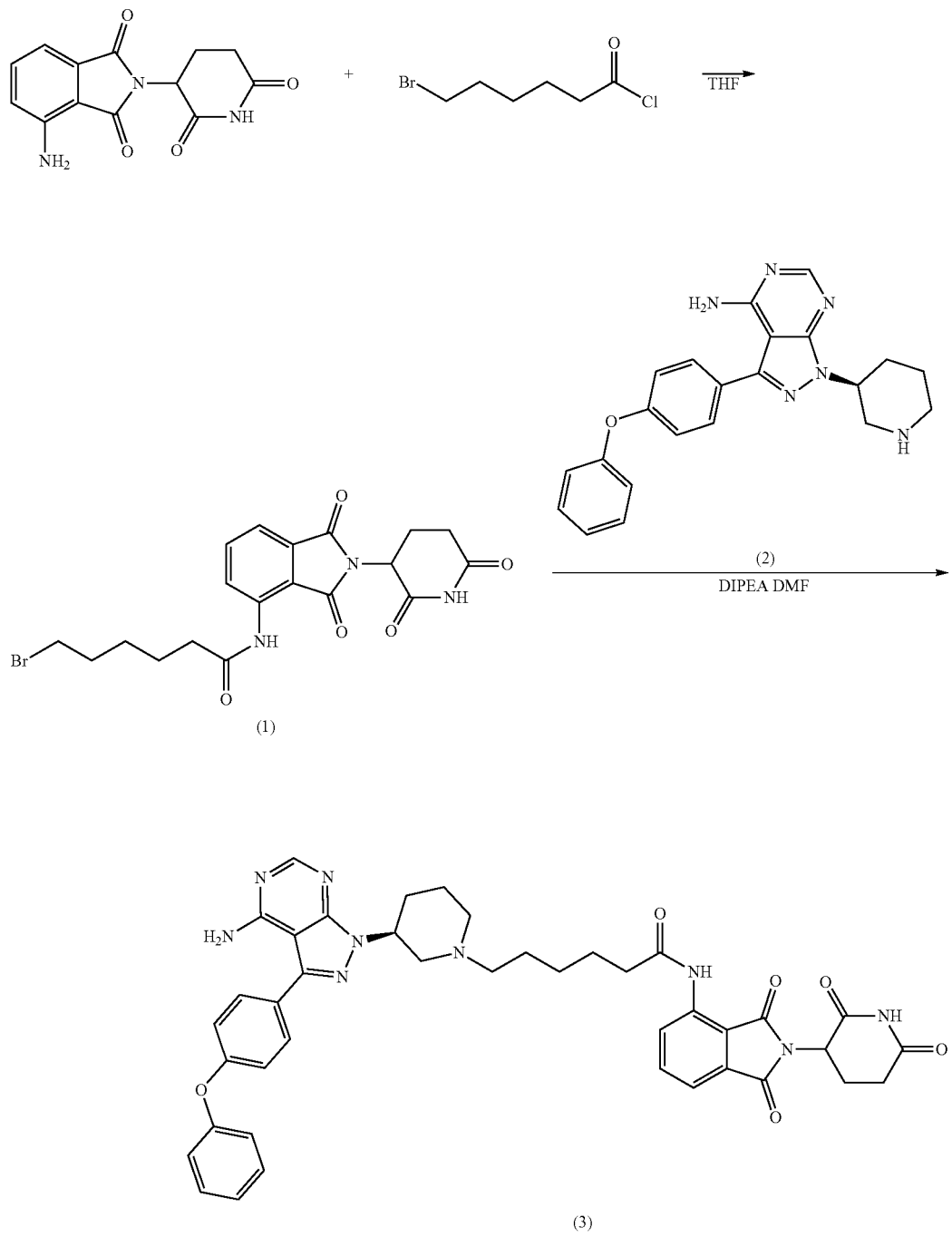

Step 1:

2.14 g of 6-bromohexanoyl chloride and 1.37 g of pomalidomide were dissolved in 50 ml of tetrahydrofuran. The mixture was stirred at reflux for 8 h, then cooled to room temperature and concentrated under vacuum at 40° C. to obtain 1.22 g of compound (1). MS (ESI): 450 [M+H]$^+$.

Step 2:

860 mg of compound (1), 1 g of compound (2) and 0.60 g of diisopropylethylamine were dissolved in 30 ml of DMF (N, N-dimethylformamide). The mixture was stirred at 80° C. for 6 h, and then cooled to room temperature. After concentration, the residue was purified by column chromatography to obtain 408 mg of compound (3) with a yield of 31.2%. MS (ESI): 756 [M+H]$^+$. $^1$H NMR (400 MHz, CDCl3) δ 10.32-10.14 (m, 1H), 9.43 (s, 1H), 8.83 (d, J=8 Hz, 1H), 8.42 (d, J=8 Hz, 1H), 7.67 (t, 1H), 8.83 (d, J=8 Hz, 2H), 7.55 (d, J=8 Hz, 1H), 7.39 (t, 3H), 7.17 (m, 3H), 7.08 (d, J=8 Hz, 2H), 5.81 (s, 2H), 5.02-4.95 (m, 2H), 3.17 (d, J=8 Hz, 1H), 2.86-2.76 (m, 2H), 2.66-2.55 (m, 1H), 2.49-2.46 (m, 3H), 2.19-2.06 (m, 3H), 1.86 (m, 2H), 1.80-1.76 (m, 2H), 1.59-1.56 (m, 2H), 1.44-1.42 (m, 2H), 1.29-1.26 (m, 1H), 0.8-0.7 (m, 1H).

Example 2 Preparation of Compound 7

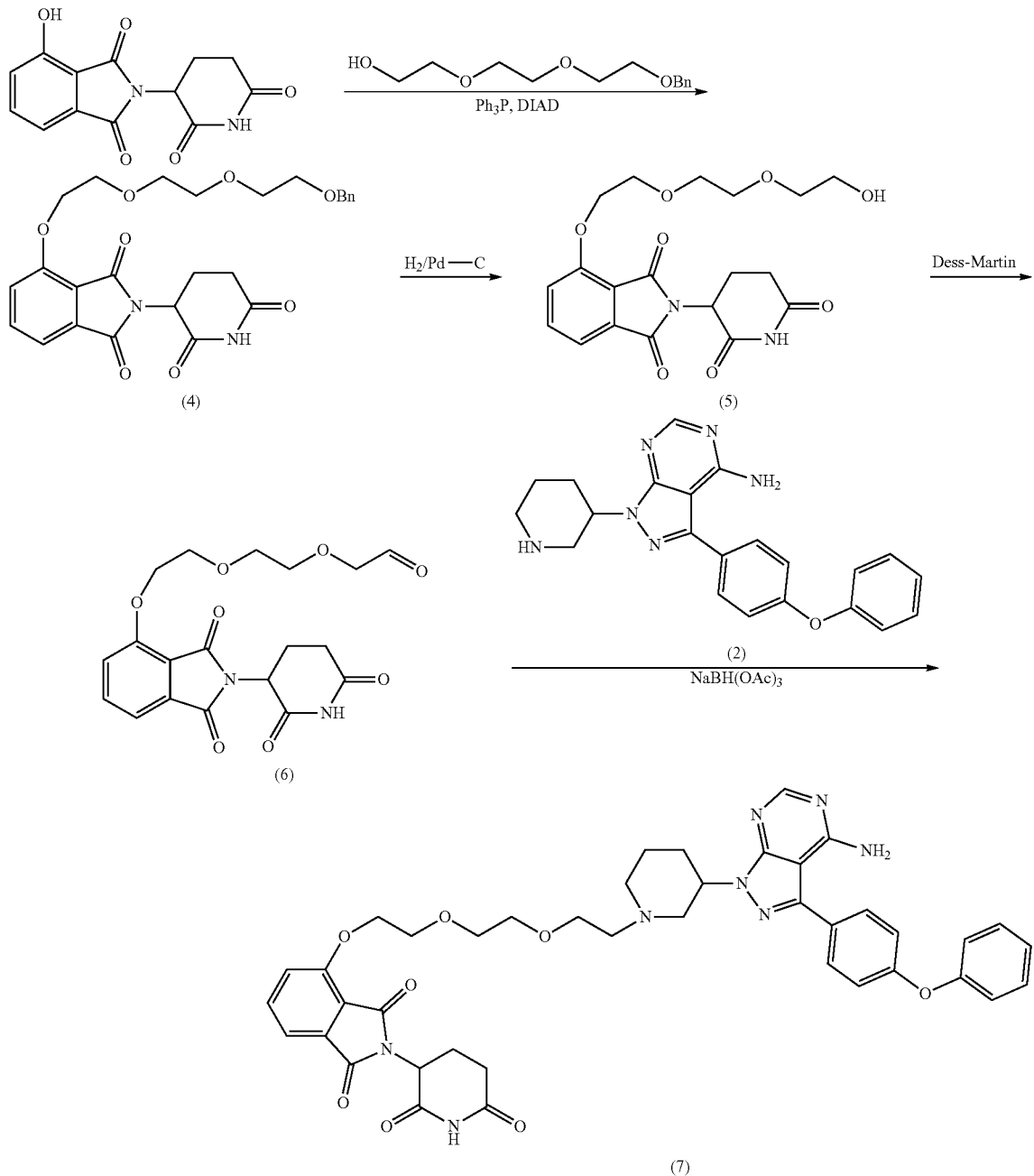

Step 1:

100 mg of 4-hydroxythalidomide, 96 mg of triethylene glycol monobenzyl ether, and 100 mg of triphenylphosphine were dissolved in 10 ml of anhydrous THF, and then 95 mg of DIAD (diisopropyl azodicarboxylate) was added dropwise. The reaction was carried out at room temperature for 2 h. THF was removed under reduced pressure, and 110 mg of compound (4) was obtained after purification by column chromatography. MS (ESI): 497 [M+H]$^+$.

Step 2:

100 mg of compound (4) and 100 mg of 10% Pd—C were added into 10 ml of methanol and the mixture was hydrogenated at room temperature overnight. Then the mixture was filtered and the filtrate was concentrated. The residue was purified by column chromatography to obtain 40 mg of compound (5). MS (ESI): 407 [M+H]$^+$.

Step 3:

30 mg of compound (5) was dissolved in 5 ml of dichloromethane, and then 47 mg of Dess-martin oxidant was added. The mixture was reacted at room temperature for 3 h. A saturated aqueous solution of NaHCO$_3$ and a saturated aqueous solution of Na$_2$S$_2$O$_3$ were added to the reaction system, and stirred for 5 min. The organic layer was separated, dry over anhydrous Na$_2$S$_2$O$_3$, and concentrate to dryness. The obtained compound (6) is directly used in the next step.

After compound (6) was dissolved in 7 ml of dichloromethane, 50 mg of raw material (2) and 30 mg of NaBH(OAc)₃ were added, and the mixture was reacted overnight at room temperature. Dichloromethane was distilled off under reduced pressure. 35 mg of compound (7) was obtained after purification by column chromatography. MS (ESI): 775 [M+H]⁺. ¹H NMR (400 MHz, CDCl3) δ 9.63-9.96 (br, 1H), 8.38 (d, J=7.6 Hz, 1H), 7.60-7.66 (m, 3H), 7.44 (d, J=7.2 Hz, 1H), 7.38 (m, 2H), 7.22 (dd, J=8.4, 1.6 Hz, 1H), 7.11-7.19 (m, 3H), 7.07 (d, J=8.4 Hz, 2H), 5.75 (br, 2H), 4.91-5.05 (m, 2H), 4.29 (t, J=4.8 Hz, 2H), 3.91 (m, 2H), 3.75 (m, 2H), 3.62 (m, 4H), 3.21 (br, 1H), 2.97 (br, 1H), 2.60-2.91 (m, 6H), 2.05-2.20 (m, 4H), 1.83 (m, 2H).

Example 3 Preparation of Compound 10

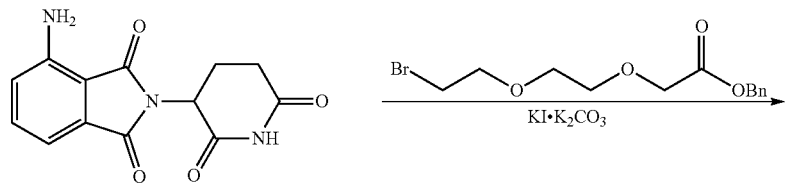

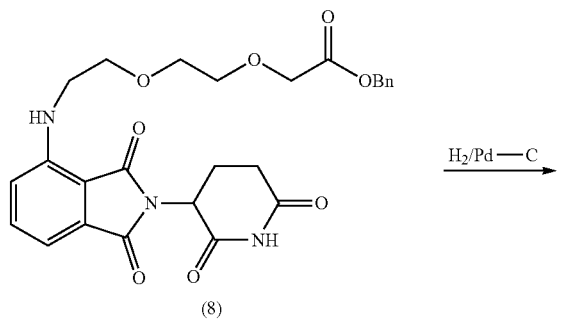

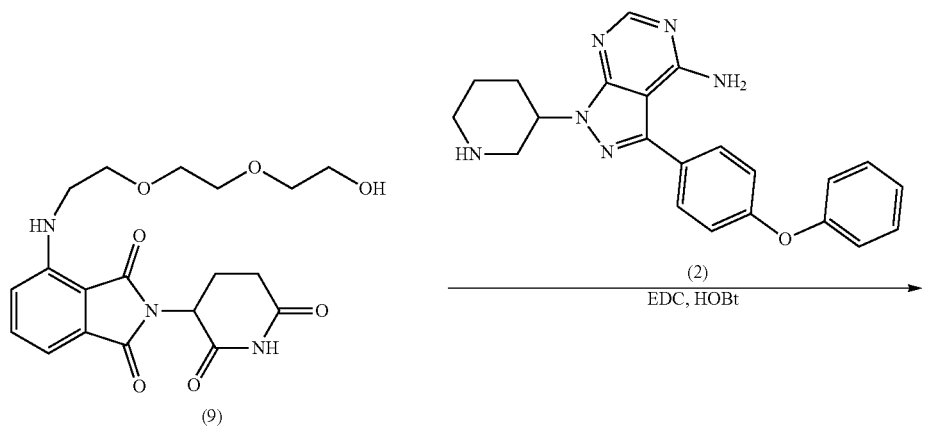

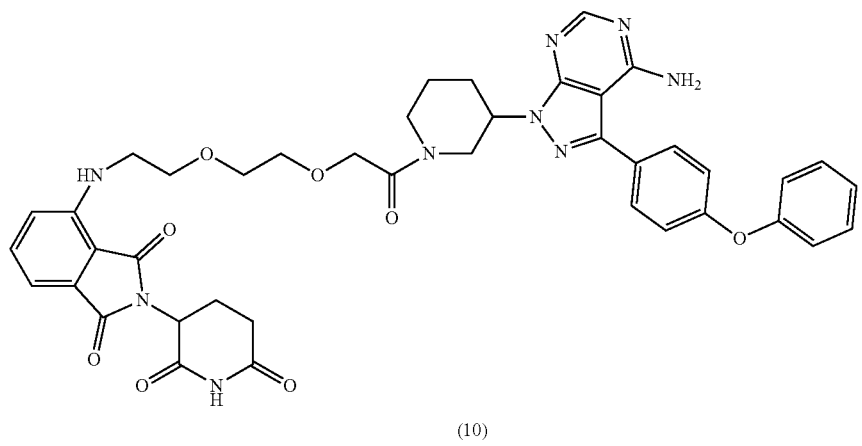

Step 1:

174 mg of benzyl 2-(2-(2-bromoethoxy)ethoxy)acetate, 100 mg of potassium carbonate, 20 mg of potassium iodide and 100 mg of pomalidomide were added into 20 ml of DMF (N, N-dimethylformamide), and reacted at 80° C. overnight. The reaction solution was purified by column chromatography to obtain 113 mg of compound (8). MS (ESI): 510 [M+H]+.

Step 2:

100 mg of compound (8) and 100 mg of 10% Pd—C were added into 10 ml of methanol and the mixture was hydrogenated at room temperature overnight. Then the mixture was filtered and the filtrate was concentrated. The residue was purified by column chromatography to obtain 73 mg of compound (9). MS (ESI anion): 418 [M+H]−.

Step 3:

50 mg of compound (9) and 50 mg of raw material (2) were dissolved in 5 ml of dichloromethane, and 20 mg of HOBt (1-hydroxybenzotriazole) and 40 mg of EDC (1-(3-dimethylaminopropyl)-3-ethyl-carbodiimide hydrochloride) were added. The mixture was reacted at room temperature overnight. Dichloromethane was distilled off under reduced pressure, and 41 mg of compound (10) was obtained after purification by column chromatography. MS (ESI): 788 [M+H]+. 1H NMR (400 MHz, CDCl3) 9.90-10.22 (br, 1H), 8.37 (d, J=7.6 Hz, 1H), 7.62 (m, 2H), 7.45 (m, 1H), 7.38 (t, J=7.6 Hz, 2H), 7.04-7.18 (m, 6H), 6.87 (d, J=8.8 Hz, 1H), 6.47 (m, 1H), 5.81 (br, 2H), 5.01 (m, 1H), 4.90 (m, 1H), 4.65 (s, 2H), 3.63-3.72 (m, 6H), 3.25 (br, 1H), 2.62-3.04 (m, 7H), 2.06-2.20 (m, 4H), 1.83 (m, 2H).

Example 4 Preparation of Compound 13

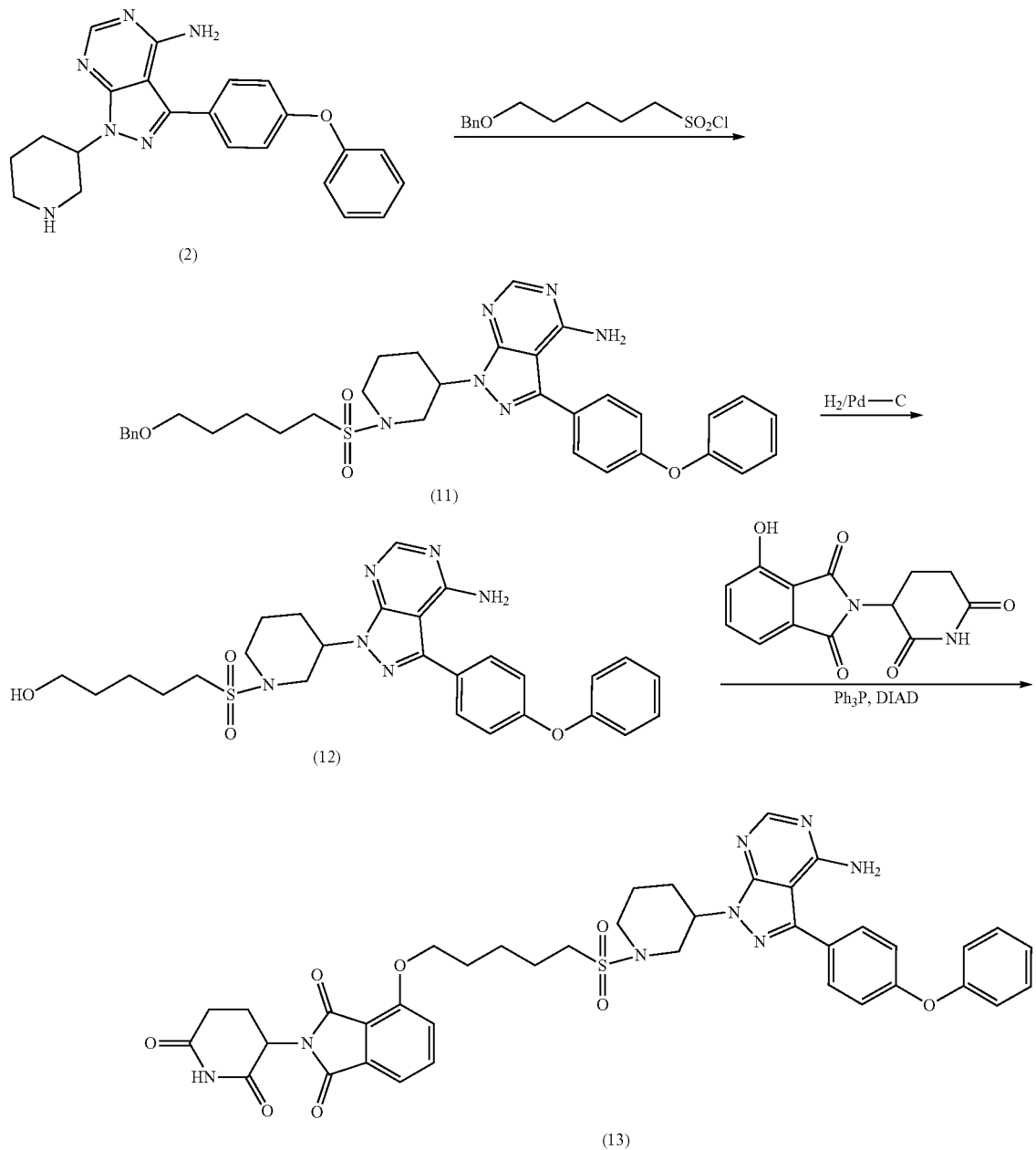

Step 1:

200 mg of the raw material (2) was dissolved in 20 ml of dichloromethane, 100 mg of triethylamine and 150 mg of 5-benzyloxypentanesulfonyl chloride were added, and the mixture was reacted at room temperature overnight. The solvent was removed under reduced pressure, and 233 mg of compound (11) was obtained after purification by column chromatography. MS (ESI): 627 [M+H]+.

Step 2:

200 mg of compound (11) and 200 mg of 10% Pd—C were added into 20 ml of methanol and the mixture was hydrogenated at room temperature overnight. Then the mixture was filtered and the filtrate was concentrated. The residue was purified by column chromatography to obtain 155 mg of compound (12). MS (ESI): 536[M+H]+.

Step 3:

50 mg of 4-hydroxythalidomide, 50 mg of triphenylphosphine and 80 mg of compound (12) were dissolved in 5 ml of anhydrous tetrahydrofuran, 50 mg of DIAD (diisopropyl azoclicarboxylate) was added dropwise, and the reaction was carried out at room temperature for 3 h. Tetrahydrofuran was removed under reduced pressure, and 41 mg of compound (13) was obtained after purification by column chromatography. MS (ESI): 793 [M+H]+. 1H NMR (400 MHz, CDCl3) δ 9.83-9.95 (br, 1H), 8.38 (d, J=7.6 Hz, 1H), 7.60-7.75 (m, 3H), 7.45 (m, 1H), 7.39 (t, J=7.2 Hz, 2H), 7.00-7.19 (m, 5H), 6.85 (d, J=8.4 Hz, 1H), 5.81 (br, 1H), 5.03 (m, 1H), 4.92 (m, 1H), 3.95 (t, J=7.2 Hz, 2H), 3.45 (m, 2H), 3.26 (br, 1H), 2.60-3.02 (m, 7H), 2.06-2.20 (m, 4H), 1.70-1.95 (m, 4H), 1.35 (br, 2H).

Similarly, the following compounds were prepared by a method similar to the above example:

| Compound No | Structure of compound | Reference example for synthesis method | MS(ESI) |
|---|---|---|---|
| 14 | | 2.3 | 774[M + H]+ |
| 15 | | 2.3 | 818[M + H]+ |
| 16 | | 2 | 819[M + H]+ |
| 17 | | 2.3 | 829[M + H]+ |

-continued

| Compound No | Structure of compound | Reference example for synthesis method | MS(ESI) |
|---|---|---|---|
| 18 | | 2.3 | 873[M + H]+ |
| 19 | | 2.3 | 887[M + H]+ |
| 20 | | 2.3 | 901[M + H]+ |

-continued

| Compound No | Structure of compound | Reference example for synthesis method | MS(ESI) |
|---|---|---|---|
| 21 | | 2.3 | 903[M + H]⁺ |
| 22 | | 2.3 | 917[M + H]⁺ |
| 23 | | 3 | 828[M + H]⁺ |
| 24 | | 3 | 872[M + H]⁺ |

-continued
| Compound No | Structure of compound | Reference example for synthesis method | MS(ESI) |
|---|---|---|---|
| 25 | 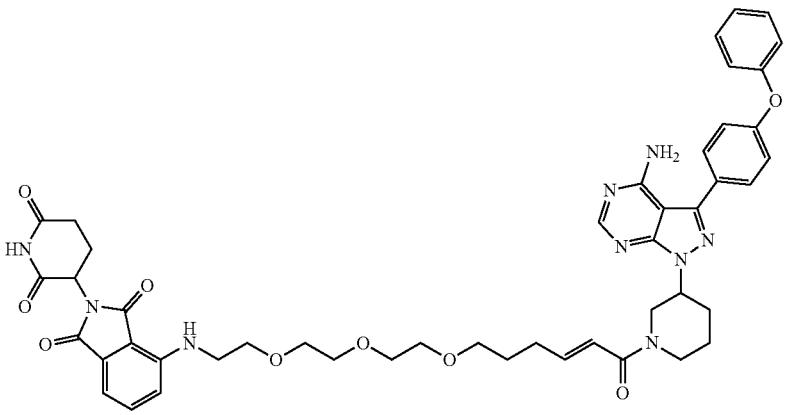 [SMILES: Nc1ncnc2c1c(-c1ccc(Oc3ccccc3)cc1)nn2C1CCCN(C(=O)/C=C/CCCOCCOCCOCCNc2cccc3c2C(=O)N(C2CCC(=O)NC2=O)C3=O)C1] | 3 | 886[M + H]⁺ |
| 26 | 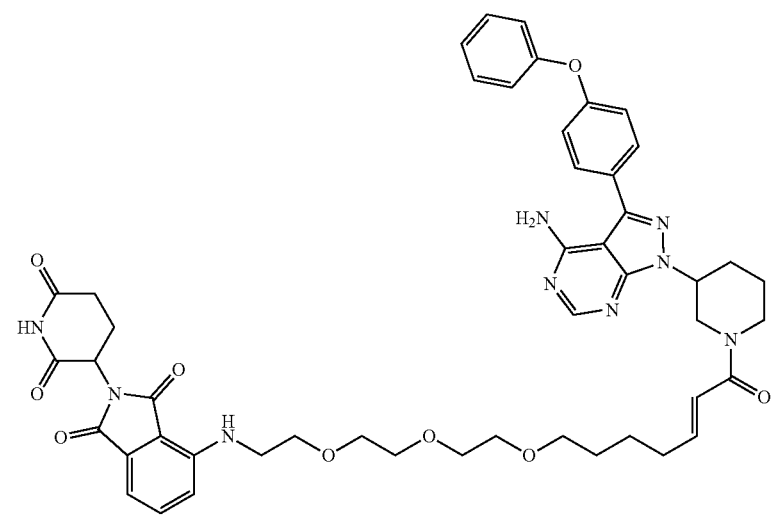 | 3 | 900[M + H]⁺ |
| 27 | 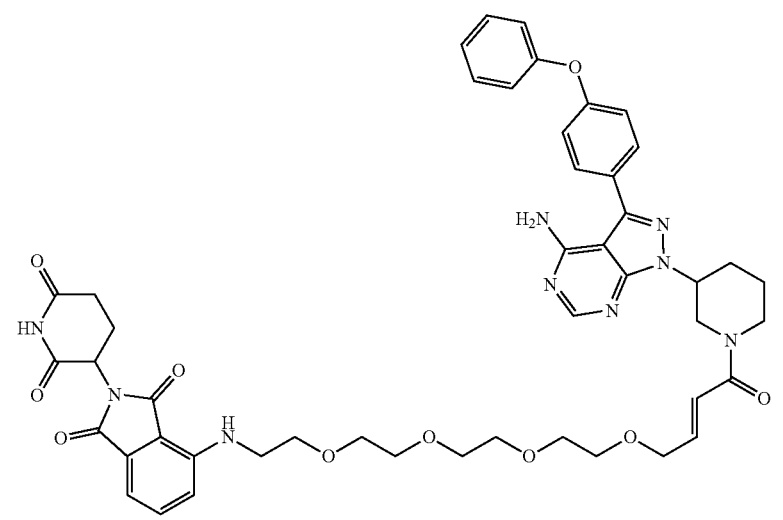 | 3 | 902[M + H]⁺ |

-continued
| Compound No | Structure of compound | Reference example for synthesis method | MS(ESI) |
|---|---|---|---|
| 28 | 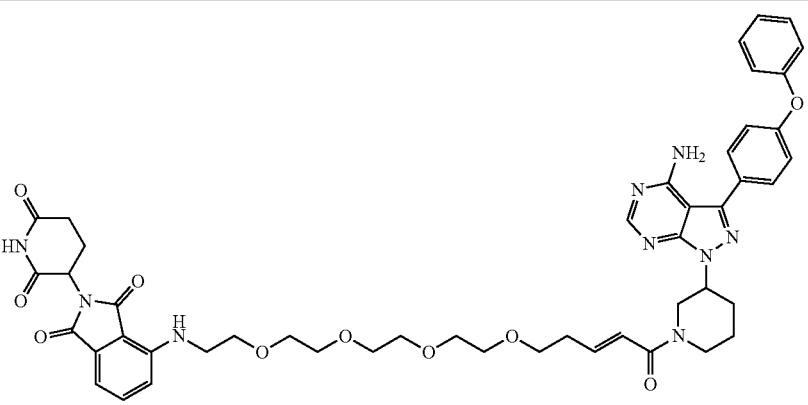 [SMILES: Nc1ncnc2c1c(-c1ccc(Oc3ccccc3)cc1)nn2C1CCCN(C(=O)/C=C/CCOCCOCCOCCOCCNc2cccc3c2C(=O)N(C2CCC(=O)NC2=O)C3=O)C1] | 3 | 916[M + H]+ |
| 29 | 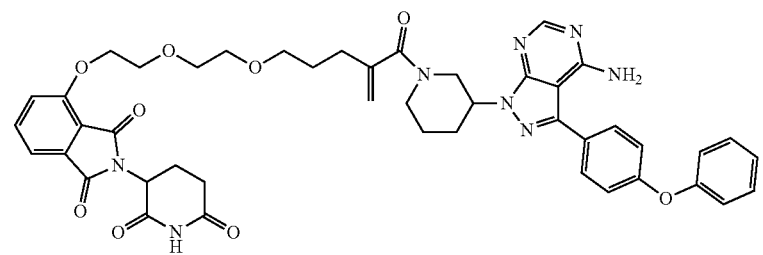 [SMILES: C=C(CCCOCCOCCOc1cccc2c1C(=O)N(C1CCC(=O)NC1=O)C2=O)C(=O)N1CCCC(n2nc(-c3ccc(Oc4ccccc4)cc3)c3c(N)ncnc32)C1] | 2.3 | 843[M + H]+ |
| 30 | 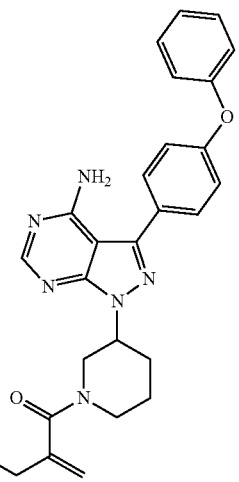 | 2.3 | 829[M + H]+ |
| 31 | 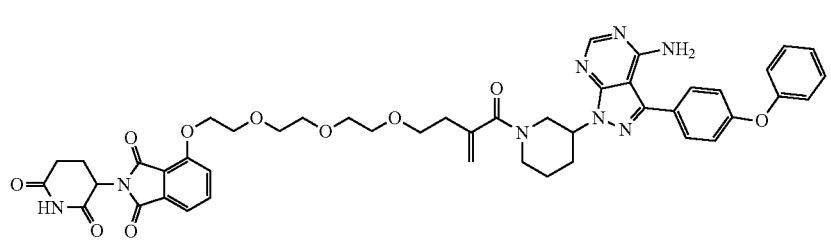 [SMILES: C=C(CCOCCOCCOCCOc1cccc2c1C(=O)N(C1CCC(=O)NC1=O)C2=O)C(=O)N1CCCC(n2nc(-c3ccc(Oc4ccccc4)cc3)c3c(N)ncnc32)C1] | 2.3 | 873[M + H]+ |

| Compound No | Structure of compound | Reference example for synthesis method | MS(ESI) |
|---|---|---|---|
| 32 | 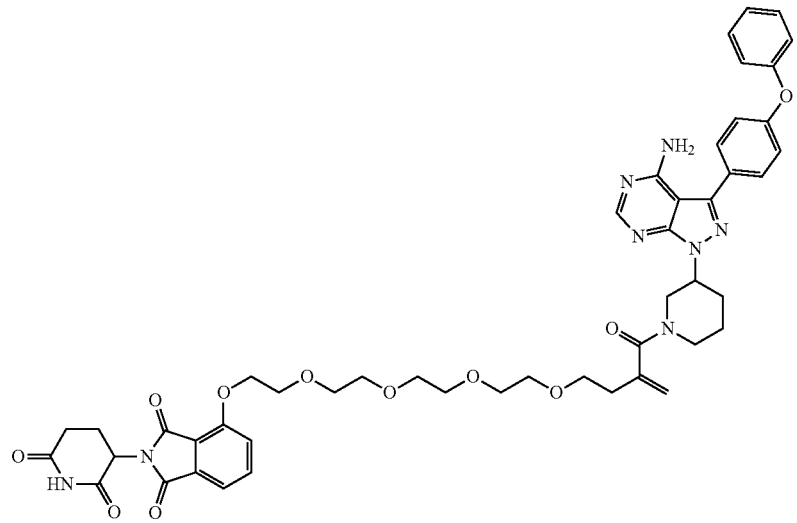 [SMILES: C=C(CCOCCOCCOCCOCCOc1cccc2c1C(=O)N(C1CCC(=O)NC1=O)C2=O)C(=O)N1CCCC(n2nc(-c3ccc(Oc4ccccc4)cc3)c3c(N)ncnc32)C1] | 2.3 | 917[M + H]+ |
| 33 | 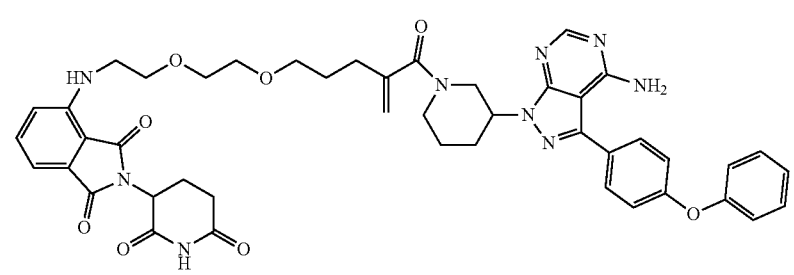 | 3 | 842[M + H]+ |
| 34 | 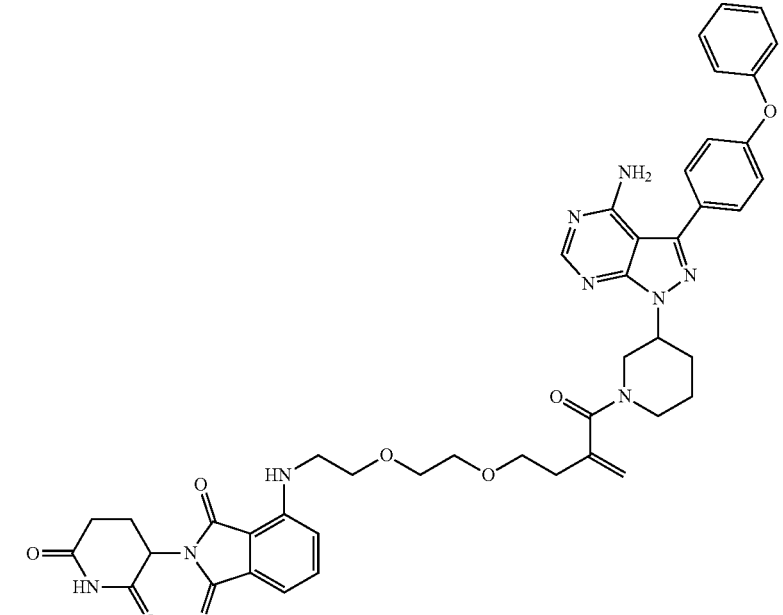 | 3 | 828[M + H]+ |

-continued

| Compound No | Structure of compound | Reference example for synthesis method | MS(ESI) |
|---|---|---|---|
| 35 | | 3 | 872[M + H]⁺ |
| 36 | | 3 | 916[M + H]⁺ |
| 37 | | 2.3 | 870[M + H]⁺ |
| 39 | | 2.3 | 914[M + H]⁺ |

-continued

| Compound No | Structure of compound | Reference example for synthesis method | MS(ESI) |
|---|---|---|---|
| 40 | | 2.3 | 958[M + H]+ |
| 41 | | 3 | 869[M + H]+ |
| 43 | | 3 | 913[M + H]+ |

| Compound No | Structure of compound | Reference example for synthesis method | MS(ESI) |
|---|---|---|---|
| 44 | | 3 | 957[M + H]⁺ |

Example 5 Testing the Inhibition Activity of Compounds on Btk by Caliper Assay The experimental steps were as follows:

Preparation of 1× kinase reaction buffer (50 mM HEPES, PH 7.5; 0.0015% Brij-35) and kinase reaction termination solution (100 mM HEPES, PH 7.5; 0.0015% Brij-35; 0.2% Coating Reagent; 50 mM EDTA);

Preparation of experimental samples: 100 μL of 5 μM sample solution (dissolved in 100% DMSO) was added to a 96-well plate to obtain a 50× sample solution. As a control, two wells were set containing only 100 μL of 100% DMSO on the same plate. One was served as a control without samples and the other was served as a control without enzymes. 10 μL of sample and 90 μL of 1× kinase reaction buffer were added to a 96-well plate as a transfer plate. The transfer plate was shaken for 10 minutes.

Preparation of the test plate: taking 5 μL each of the prepared samples in the 96-well transfer plate into a 384-well plate.

Kinase reaction: to 5 μL of 5× compound solution (dissolved in DMSO, diluted 10 times with water) was added 10 μL of 2.5× Btk kinase solution (kinase was diluted with 1× kinase reaction buffer), and incubated at room temperature for 10 min, then 10 μL of 2.5× substrate peptide solution (FAM-labeled peptide and ATP were diluted with 1× kinase reaction buffer) was added.

Termination of the kinase reaction: 25 μL of kinase termination solution was added after being reacted at 28° C. for a period of time.

The fluorescence (F) was tested on a Caliper and data was collected.

The inhibition rate of kinase activity was calculated: the percent inhibition rate of kinase activity=($F_{DMSO\ control}$−$F_{sample}$)/($F_{DMSO\ control}$−$F_{negative\ control}$)×100, with DMSO as the solution control, and no kinase as the negative control.

The results show that the inhibitory activity of compound (100 nM) on Btk is shown in the following table:

| Compound No. | Inhibition(%) |
|---|---|
| 3 | 92 |
| 7 | 99 |
| 14 | 99 |
| 15 | 98 |
| 16 | 95 |

Example 6 Testing the Btk Protein Degradation Activity of Compounds by Western Blot Cell lines: RPMI8226 Cell line was cultured in RPMI1640 medium containing 10% calf serum in a 37° C., 5% $CO_2$, and saturated humidity incubator.

DMSO control group and compound intervention group (10 μM) were set. Cells was collected after the treatment for 24 hours, then 100 μL of pre-chilled cell lysate was added and cells were lysed on ice for 30 minutes. Total cell protein was extracted, and protein concentration was determined and quantified by cliquinolinecarboxylic acid (BCA) method. After routine gelatinization, loading, electrophoresis, then transferring to membrane and blocking, rabbit anti-human Btk (1:500) was added, and incubated at 4° C. overnight. The mixture was rinsed and then horseradish peroxidase labeled goat anti-rabbit IgG (1:5000) was added. After the rinsing it was developed by the ECL developing solution, the Bio-Rad gel imaging system was used for scanning and imaging, and the computer software was used for analysis. Glycerol phosphate dehydrogenase (GAPDH) was used as an internal control.

Image J software was used to analyze the gray scale of each band to calculate the Btk protein degradation rate of the compound.

The results show that the degradation activity of the compound (10 μM) on Btk protein in RPMI8226 cells is shown in the following table:

| Compound No. | Degradation activity |
|---|---|
| 3 | ++++ |
| 7 | ++++ |
| 14 | ++++ |
| 15 | ++++ |
| 16 | ++++ |
| 17 | +++ |
| 18 | +++ |
| 19 | +++ |
| 20 | +++ |
| 21 | +++ |
| 22 | +++ |
| 23 | ++++ |
| 24 | ++++ |
| 25 | ++++ |
| 26 | ++++ |
| 27 | ++++ |
| 28 | +++ |
| 29 | ++++ |
| 30 | ++++ |
| 31 | ++++ |
| 32 | +++ |
| 33 | ++++ |
| 34 | ++++ |
| 35 | ++++ |
| 36 | +++ |
| 37 | ++++ |
| 39 | ++++ |
| 40 | +++ |
| 41 | +++ |
| 43 | ++++ |
| 44 | +++ |
| control compound | − |

Note:
in the above table, "−" represents no degradation activity, "+" represents a degradation rate of 10%-30%, "++" represents a degradation rate of 30%-50%, and "+++" represents a degradation rate of 50%-90%, and "++++" means the degradation rate is greater than 90%.

The structure of the control compound is as follows:

Example 7 Testing the Inhibitory Effect of Formula Compounds on the Proliferation of RPMI 8226 Cells (Human Multiple Myeloma Cells) by CCK8 Assay The inhibitory effect of the compound on the proliferation of RPMI 8226 cells (commercially available from ATCC) was determined by the CCK8 assay in vitro. The experimental steps were as follows:

RPMI 8226 cells were cultured in 1640 medium containing 10% calf serum, seeded in a 96-well plate with $2\times10^5$ cells/well, and placed in a 37° C., 5% $CO_2$ incubator. The compound was dissolved in dimethyl sulfoxide (DMSO) to obtain a solution with a concentration of 10 mM, and then diluted to the desired concentration with a phosphate buffer solution. The solution was added to the above 96-well plate. Each concentration has 2 wells with 10 μl per well. Each concentration was tested in duplicate. As a control, DMSO was diluted in the corresponding gradient and then added to the plate.

After the 96-well plate was cultured in a 37° C., 5% $CO_2$ cell incubator for 48 hours, 10 μl of CCK8 solution was added to each well, and it was cultured in the incubator for another 1 to 4 hours. The light absorption value at 465 nm was measured.

The relative survival rate of the cells after the compound treatment was calculated based on the light absorption value.

The $IC_{50}$ of the compound against RPMI 8226 cells was calculated by software.

The inhibitory effect of synthesized compounds on RPMI 8226 cells in vitro is shown in the following table:

| Compound No. | $IC_{50}$ (μM) |
|---|---|
| 3 | 34 |
| 7 | 83 |
| 14 | 6 |

Activity test data shows that the compounds of the present invention have significant inhibitory activity on Ibrutinib-resistant cell lines, so the compounds of the present invention can be used to treat Ibrutinib-resistant tumors.

Example 8 Testing the Inhibitory Effect of Formula Compounds on the Proliferation of DOHH2 Cells (Human B Cell Lymphoma Cells) and SU-DHL-6 (Human B Cell Lymphoma Cells) by CTG Assay The CCK8 assay was used to determine the inhibitory effect of the compounds on the proliferation of DOHH2 cells

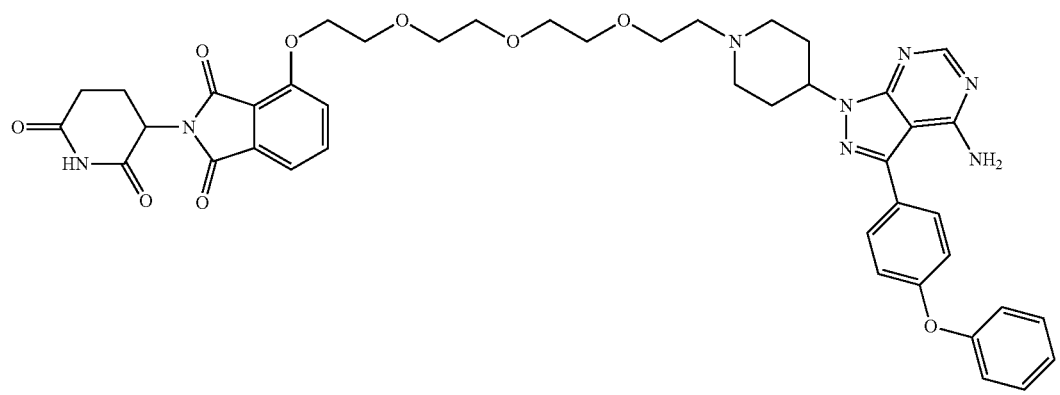 [SMILES: Nc1ncnc2c1c(-c1ccc(Oc3ccccc3)cc1)nn2C1CCN(CCOCCOCCOCCOc2cccc3c2C(=O)N(C2CCC(=O)NC2=O)C3=O)CC1]

(available from ATCC) and SU-DHL-6 cells (available from ATCC) in vitro. Cells were cultured and compounds were prepared referring to Example 7. The cell plating density was 1×10⁴ cells/well for DOHH2 cells, and 1.5×10⁴ cells/well for SU-DHL-6 cells. The culture time after the administration was 72 hours. After that an appropriate amount of CTG reagent was added, the luminescence value was measured, and the inhibition rate was calculated.

The inhibitory effect of the synthesized compound (10 μM) on DOHH2 and SU-DHL-6 cells in vitro is shown in the table below.

| Compound No. | Inhibition(%) | |
| --- | --- | --- |
| | DOHH2 | SU-DHL-6 |
| 3 | 87% | 60% |
| 7 | 63% | 53% |
| 14 | 98% | 87% |
| 15 | 99% | 94% |
| 16 | 84% | 71% |

All publications mentioned herein are incorporated by reference as if each individual document is cited as a reference, as in the present application. It should also be understood that, after reading the above teachings of the present invention, those skilled in the art can make various changes or modifications, equivalents of which fall in the scope of claims as defined in the appended claims.

What is claimed:

1. A compound represented by Formula I':

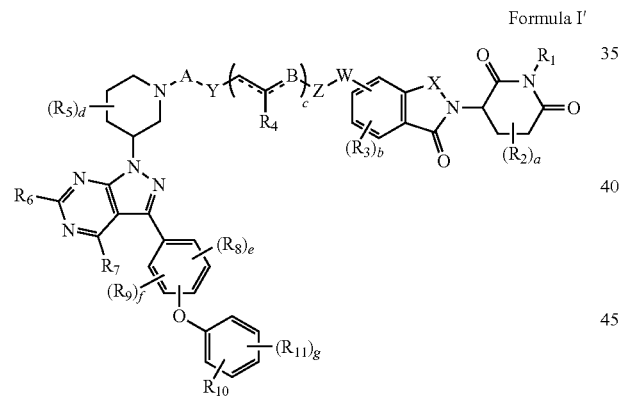

Formula I' or a pharmaceutically acceptable salt thereof, wherein:
  each ------- is independently a single or double bond;
  A is absent;
  B is —O—;
  W is —NR$_{17}$— or —O—;
  X is —C(O)—;
  each X$_6$ is independently absent, NR$_{32}$, O, or S;
  Y is —(CR$_{22}$R$_{23}$)$_h$—;
  Z is —(CR$_{24}$R$_{25}$)$_i$—;
  R$_1$ is H, C$_{1-8}$ alkyl, C$_{2-8}$ alkenyl, C$_{2-8}$ alkynyl, C(O)H, C(O)C$_{1-6}$ hydrocarbyl, C$_{3-8}$ cycloalkyl, C$_{3-8}$ cycloalkenyl, heterocyclic hydrocarbyl, or phenyl, wherein the heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, C(O)C$_{1-6}$ hydrocarbyl, C$_{3-8}$ cycloalkyl, C$_{3-8}$ cycloalkenyl, heterocyclic hydrocarbyl, or phenyl is optionally substituted;

each R$_2$ is independently H, F, Cl, Br, I, CN, C$_{1-8}$ alkyl, C$_{2-8}$ alkenyl, C$_{2-8}$ alkynyl, C(O)H, C(O)C$_{1-6}$ hydrocarbyl, C(O)NH$_2$, C(O)NHC$_{1-6}$ hydrocarbyl, C(O)N(C$_{1-6}$ hydrocarbyl)$_2$, NR$_{34}$R$_{35}$, OR$_{33}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, C(O)C$_{1-6}$ hydrocarbyl, C(O)NHC$_{1-6}$ hydrocarbyl, C(O)N(C$_{1-6}$ hydrocarbyl)$_2$, cyclic hydrocarbyl, and heterocyclic hydrocarbyl is optionally and independently substituted;

each R$_3$ is independently H, F, Cl, Br, I, CN, NO$_2$, C$_{1-8}$ alkyl, C$_{2-8}$ alkenyl, C$_{2-8}$ alkynyl, NR$_{28}$R$_{29}$, OR$_{27}$, X$_6$C(O)R$_{31}$, X$_6$S(O)$_k$R$_{30}$ cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, cyclic hydrocarbyl, and heterocyclic hydrocarbyl is optionally and independently substituted;

each R$_4$ is independently H, CN, C$_{1-8}$ alkyl, C$_{2-8}$ alkenyl, C$_{2-8}$ alkynyl, C(O)OH, or C(O)O(hydrocarbyl), wherein each C$_{1-8}$ alkyl, C$_{2-8}$ alkenyl, C$_{2-8}$ alkynyl, and C(O)O(hydrocarbyl) is optionally and independently substituted;

each R$_5$ is independently H, F, Cl, Br, I, CN, C$_{1-8}$ alkyl, C$_{2-8}$ alkenyl, C$_{2-8}$ alkynyl, C(O)H, C(O)C$_{1-6}$ hydrocarbyl, C(O)NH$_2$, C(O)NHC$_{1-6}$ hydrocarbyl, C(O)N(C$_{1-6}$ hydrocarbyl)$_2$, NR$_{34}$R$_{35}$, OR$_{33}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, C(O)C$_{1-6}$ hydrocarbyl, C(O)NHC$_{1-6}$ hydrocarbyl, C(O)N(C$_{1-6}$ hydrocarbyl)$_2$, cyclic hydrocarbyl, and heterocyclic hydrocarbyl is optionally and independently substituted;

R$_6$ is H, F, Cl, Br, I, CN, NO$_2$, C$_{1-8}$ alkyl, C$_{2-8}$ alkenyl, C$_{2-8}$ alkynyl, NR$_{28}$R$_{29}$, OR$_{27}$, X$_6$C(O)R$_{31}$, X$_6$S(O)$_k$R$_{30}$, cyclic hydrocarbyl, or heterocyclic hydrocarbyl, wherein the heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, cyclic hydrocarbyl, or heterocyclic hydrocarbyl is optionally substituted;

R$_7$ is NR$_{28}$R$_{29}$;

each R$_8$ is independently H, F, Cl, Br, I, CN, NO$_2$, C$_{1-8}$ alkyl, C$_{2-8}$ alkenyl, C$_{2-8}$ alkynyl, NR$_{28}$R$_{29}$, OR$_{27}$, X$_6$C(O)R$_{31}$, X$_6$S(O)$_k$R$_{30}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, cyclic hydrocarbyl, and heterocyclic hydrocarbyl is optionally and independently substituted;

each R$_9$ is independently H, F, Cl, Br, I, CN, NO$_2$, C$_{1-8}$ alkyl, C$_{2-8}$ alkenyl, C$_{2-8}$ alkynyl, NR$_{28}$R$_{29}$, OR$_{27}$, X$_6$C(O)R$_{31}$, X$_6$S(O)$_k$R$_{30}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

$R_{10}$ is H, F, Cl, Br, I, CN, $NO_2$, $C_{1-8}$ alkyl, $C_{2-8}$ alkenyl, $C_{2-8}$ alkynyl, $NR_{28}R_{29}$, $OR_{27}$, $X_6C(O)R_{31}$, $X_6S(O)_kR_{30}$, cyclic hydrocarbyl, or heterocyclic hydrocarbyl, wherein the heterocyclic hydrocarbyl contains one or more heteroatoms independently selected from the group consisting of nitrogen, oxygen, and sulfur, and further wherein the $C_{1-8}$ alkyl, $C_{2-8}$ alkenyl, $C_{2-8}$ alkynyl, cyclic hydrocarbyl, or heterocyclic hydrocarbyl is optionally substituted;

each $R_{11}$ is independently H, F, Cl, Br, I, CN, $NO_2$, $C_{1-8}$ alkyl, $C_{2-8}$ alkenyl, $C_{2-8}$ alkynyl, $NR_{28}R_{29}$, $OR_{27}$, $X_6C(O)R_{31}$, $X_6S(O)_kR_{30}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

$R_{17}$ is H, $C_{1-8}$ alkyl, $C_{2-8}$ alkenyl, $C_{2-8}$ alkynyl, $C_{3-8}$ cycloalkyl, $C_{3-8}$ cycloalkenyl, $C_{1-8}$ heterocyclic hydrocarbyl, or phenyl, wherein the $C_{1-8}$ heterocyclic hydrocarbyl contains one or more heteroatoms independently selected from the group consisting of nitrogen, oxygen, and sulfur, and further wherein the $C_{1-8}$ alkyl, $C_{2-8}$ alkenyl, $C_{2-8}$ alkynyl, $C_{3-8}$ cycloalkyl, $C_{3-8}$ cycloalkenyl, $C_{1-8}$ heterocyclic hydrocarbyl, or phenyl is optionally substituted;

$R_{22}$ is H, CN, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, OH, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, or phenyl, wherein the $C_{1-8}$ heterocyclic hydrocarbyl contains one or more heteroatoms independently selected from the group consisting of nitrogen, oxygen, and sulfur, and further wherein the $C_{1-8}$ alkyl, $C_{2-8}$ alkenyl, $C_{2-8}$ alkynyl, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, or phenyl is optionally substituted;

$R_{23}$ is H, CN, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, OH, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, or phenyl, wherein the $C_{1-8}$ heterocyclic hydrocarbyl contains one or more heteroatoms independently selected from the group consisting of nitrogen, oxygen, and sulfur, and further wherein the $C_{1-8}$ alkyl, $C_{2-8}$ alkenyl, $C_{2-8}$ alkynyl, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, or phenyl is optionally substituted;

each $R_{24}$ is independently H, CN, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, OH, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, or phenyl, wherein each $C_{1-8}$ heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, and phenyl is optionally and independently substituted;

each $R_{25}$ is independently H, CN, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, OH, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, or phenyl, wherein each $C_{1-8}$ heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $OC_{1-8}$ alkyl, $OC_{2-8}$ alkenyl, $OC_{2-8}$ alkynyl, $OC_{3-8}$ cycloalkyl, $OC_{3-8}$ cycloalkenyl, Ophenyl, $C_{3-8}$ cycloalkyl, $C_{3-8}$ cycloalkenyl, $C_{1-8}$ heterocyclic hydrocarbyl, and phenyl is optionally and independently substituted;

each $R_{27}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{28}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{29}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{30}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{31}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{32}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{33}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{34}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

each $R_{35}$ is independently H, $C_{1-8}$ alkyl, $C_{2-8}$ alkenyl, $C_{2-8}$ alkynyl, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, cyclic hydrocarbyl, and heterocyclic hydrocarbyl is optionally and independently substituted;

a is 0, 1, 2, 3, 4, or 5;

b is 0, 1, 2, or 3;

c is 1, 2, 3, 4, 5, 6, 7, 8, or 9;

d is 0, 1, 2, 3, 4, 5, 6, 7, 8, or 9;

e is 0, 1, 2, or 3;

f is 0, 1, 2, or 3;

g is 0, 1, or 2;

h is 0;

i is 1, 2, 3, 4, 5, or 6; and k is 0, 1, or 2;

wherein the optional substituents for $R_1$, $R_2$, $R_3$, $R_4$, $R_5$, $R_6$, $R_8$, $R_9$, $R_{10}$, $R_{11}$, $R_{17}$, $R_{22}$, $R_{23}$, $R_{24}$, $R_{25}$, $R_{27}$, $R_{28}$, $R_{29}$, $R_{30}$, $R_{31}$, $R_{32}$, $R_{33}$, $R_{34}$, and $R_{35}$ are independently selected from the group consisting of F, Cl, Br, I, CN, $C_{1-6}$ halohydrocarbyl, C(O)H, C(O)$C_{1-6}$ hydrocarbyl, $NH_2$, NH($C_{1-6}$ hydrocarbyl), N($C_{1-6}$ hydrocarbyl)$_2$, OH, O($C_{1-6}$ hydrocarbyl), and S(O)$_2C_{1-6}$ hydrocarbyl.

2. The compound according to claim 1, or a pharmaceutically acceptable salt thereof, wherein:

(i) W is —$NR_{17}$—;

$R_{17}$ is H, $C_{1-4}$ alkyl, $C_{2-4}$ alkenyl, or $C_{2-4}$ alkynyl, wherein the $C_{1-4}$ alkyl, $C_{2-4}$ alkenyl, or $C_{2-4}$ alkynyl is optionally substituted;

Z is —$(CR_{24}R_{25})_i$—;

each $R_{24}$ is independently H, $C_{1-4}$ alkyl, $C_{2-4}$ alkenyl, $C_{2-4}$ alkynyl, or OH, wherein each $C_{1-4}$ alkyl, $C_{2-4}$ alkenyl, and $C_{2-4}$ alkynyl is optionally and independently substituted;

each $R_{25}$ is independently H, $C_{1-4}$ alkyl, $C_{2-4}$ alkenyl, $C_{2-4}$ alkynyl, or OH, wherein each $C_{1-4}$ alkyl, $C_{2-4}$ alkenyl, and $C_{2-4}$ alkynyl is optionally and independently substituted; and i is 1, 2, 3, or 4; or (ii) W is —O—;

Z is —$(CR_{24}R_{25})_i$—;

each $R_{24}$ is independently H, $C_{1-4}$ alkyl, $C_{2-4}$ alkenyl, $C_{2-4}$ alkynyl, or OH, wherein each $C_{1-4}$ alkyl, $C_{2-4}$ alkenyl, and $C_{2-4}$ alkynyl is optionally and independently substituted;

each $R_{25}$ is independently H, $C_{1-4}$ alkyl, $C_{2-4}$ alkenyl, $C_{2-4}$ alkynyl, or OH, wherein each $C_{1-4}$ alkyl, $C_{2-4}$ alkenyl, and $C_{2-4}$ alkynyl is optionally and independently substituted; and i is 1, 2, or 3.

3. The compound according to claim 1, or a pharmaceutically acceptable salt thereof, wherein $R_1$ is H or $C_{1-4}$ alkyl, wherein the $C_{1-4}$ alkyl is optionally substituted.

4. The compound according to claim 1, or a pharmaceutically acceptable salt thereof, wherein each $R_4$ is independently H, CN, or $C_{1-6}$ alkyl, wherein each $C_{1-6}$ alkyl is optionally and independently substituted.

5. The compound according to claim 1, wherein the compound is selected from the group consisting of:

Compound No. 7
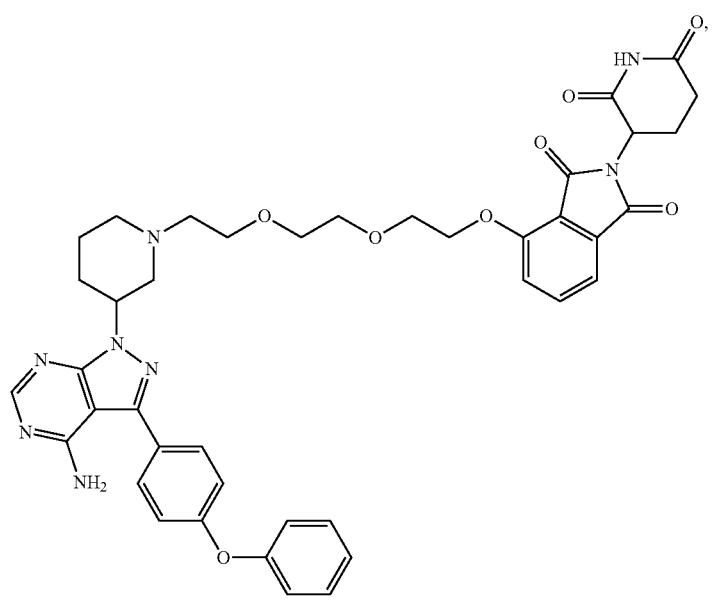
Compound No. 14
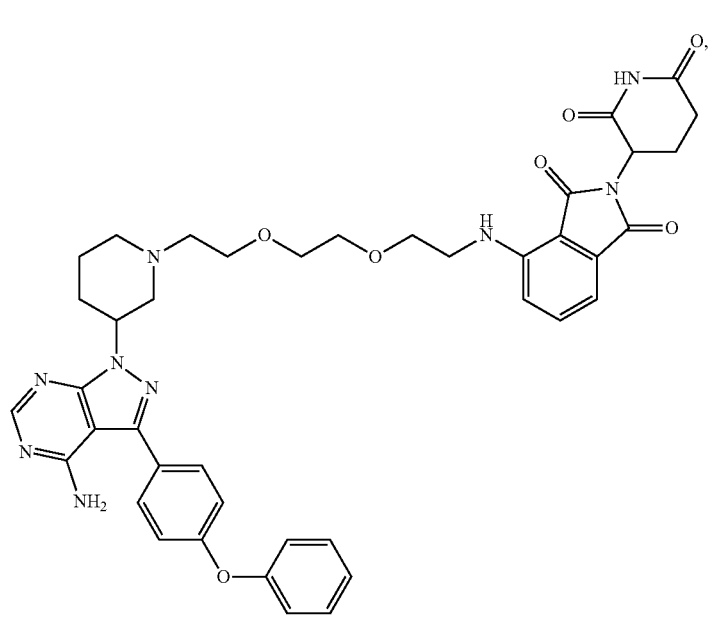
Compound No. 15
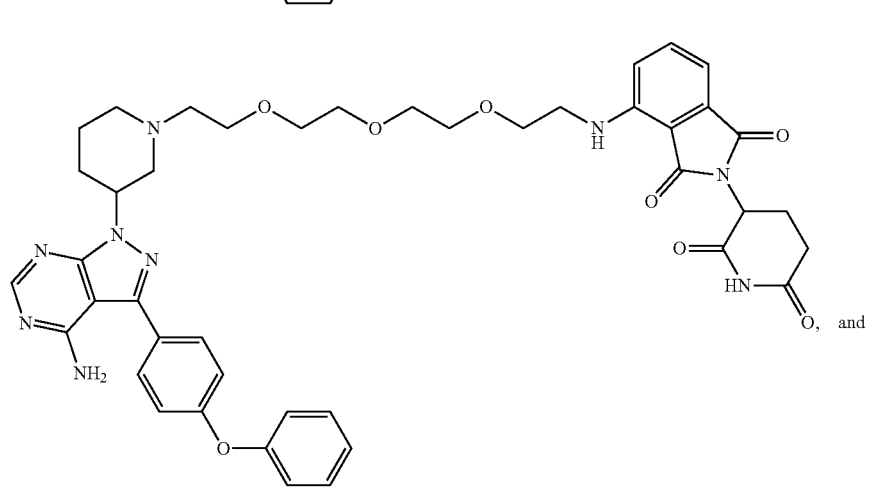
, and Compound No. 16

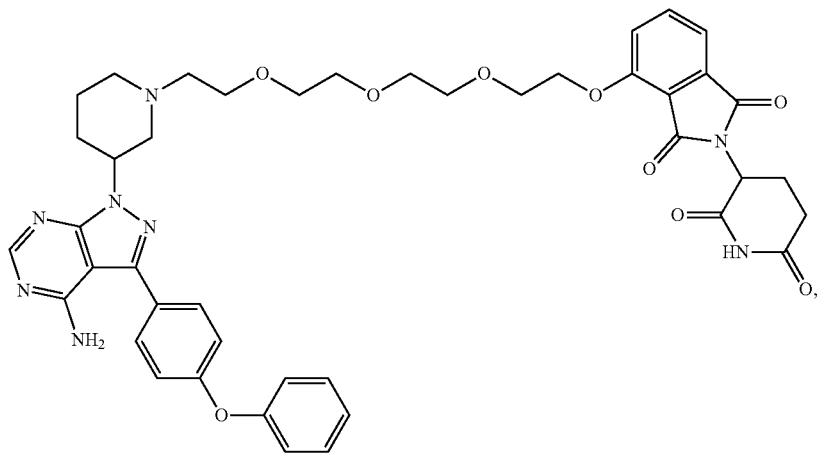

or a pharmaceutically acceptable salt thereof.

6. A pharmaceutical composition comprising a pharmaceutically acceptable carrier and the compound according to claim 1, or a pharmaceutically acceptable salt thereof.

7. A medicament comprising the compound according to claim 1, or a pharmaceutically acceptable salt thereof.

8. A method for inhibiting tumor cell proliferation in vitro, comprising contacting the tumor cell with the compound according to claim 1, or a pharmaceutically acceptable salt thereof, or the pharmaceutical composition according to claim 6.

9. The method according to claim 8, wherein the tumor cell is related to a disease selected from the group consisting of B-cell lymphoma, chronic lymphocytic leukemia, and non-Hodgkin's lymphoma.

10. A method for modulating Bruton's tyrose kinase activity in a subject, comprising administering to the subject in need thereof a therapeutically effective amount of the compound according to claim 1, or a pharmaceutically acceptable salt thereof, or the pharmaceutical composition according to claim 6.

11. The method according to claim 10, wherein the subject has an autoimmune disease or a tumor.

12. The method according to claim 11, wherein the autoimmune disease is selected from the group consisting of psoriasis and rheumatoid arthritis.

13. The method of claim 11, wherein the tumor is related to a disease selected from the group consisting of B-cell lymphoma, chronic lymphocytic leukemia, and non-Hodgkin's lymphoma.

* * * * *